United States Patent
Kim et al.

(10) Patent No.: US 12,228,575 B2
(45) Date of Patent: Feb. 18, 2025

(54) BIOMARKER COMPOSITION FOR PREDICTING CANCER MALIGNANT PROGNOSIS INDUCED BY MICROPLASTIC EXPOSURE

(71) Applicant: KOREA INSTITUTE OF RADIOLOGICAL & MEDICAL SCIENCES, Seoul (KR)

(72) Inventors: Jin Su Kim, Seoul (KR); Hyeongi Kim, Seoul (KR); Javeria Zaheer, Seoul (KR)

(73) Assignee: KOREA INSTITUTE OF RADIOLOGICAL & MEDICAL SCIENCES, Seoul (KR)

( * ) Notice: Subject to any disclaimer, the term of this patent is extended or adjusted under 35 U.S.C. 154(b) by 148 days.

(21) Appl. No.: 17/214,966

(22) Filed: Mar. 29, 2021

(65) Prior Publication Data
US 2021/0301351 A1  Sep. 30, 2021

(30) Foreign Application Priority Data

Mar. 30, 2020  (KR) ........................ 10-2020-0038278

(51) Int. Cl.
*C12Q 1/6886* (2018.01)
*G01N 33/574* (2006.01)

(52) U.S. Cl.
CPC ..... *G01N 33/57446* (2013.01); *C12Q 1/6886* (2013.01); *G01N 33/574* (2013.01); *C12Q 2600/112* (2013.01); *C12Q 2600/118* (2013.01); *C12Q 2600/158* (2013.01); *G01N 2333/70532* (2013.01); *G01N 2333/70585* (2013.01); *G01N 2333/70596* (2013.01); *G01N 2333/726* (2013.01); *G01N 2333/91017* (2013.01)

(58) Field of Classification Search
CPC .............................................. G01N 33/57446
USPC .................................................... 435/7.23
See application file for complete search history.

(56) References Cited

U.S. PATENT DOCUMENTS

2010/0113297 A1   5/2010   Lidereau et al.

FOREIGN PATENT DOCUMENTS

| CN | 109844534 A | 6/2019 |
|---|---|---|
| KR | 10-2013-0109600 A | 10/2013 |
| KR | 10-2018-0077806 A | 7/2018 |
| KR | 10-1933695 B1 | 12/2018 |
| WO | 2017/203444 A1 | 11/2017 |
| WO | 2019/016422 A1 | 1/2019 |

OTHER PUBLICATIONS

Katayama et al (Br J Cancer, 1994, 69: 580-585).*
Takada et al (Journal of Thoracic Oncology, 2016, 11(11): 1879-1890).*
Zhang et al (Environ Sci Technol, 2020, 54: 3740-3751).*
Klein et al (Science of the Total Environment, 2019, 685: 96-103).*
Qing et al (Drug Design, Development and Therapy, 2015, 9: 901-909).*
Lee et al (Scientific Reports, 2019, 9(10145): 1-9).*
Yamamoto et al (Oncology Letters, 2010, 501-505).*
Etzioni et al (Nature Reviews, 2003, 3: internet pp. 1-10).*
Mercer (Immunol Ser, 1990, 53: 39-54).*
Mayer et al (The Lancet, 1993, 342: 1019-1022).*
Jun et al (International Journal of Surgery, 2014, 12: 156-162).*
Guang-Jie Zhu et al., "Role of epithelial-mesenchymal transition markers E-cadherin, N-cadherin, β-catenin and ZEB2 in laryngeal squamous cell carcinoma", Oncology Letters 15: 3472-3481, 2018.
Giacomo Limonta et al., "Microplastics induce transcriptional changes, immune response and behavioral alterations in adult zebrafish", Scientific Reports vol. 9, Article No. 15775 (2019).
Mustafa Kahtan Al-Bayaty et al., "E-Cadherin Protein as a Potential Marker for Gastric Cancer and Its Association with Helicobacter Pylori-Induced Gastritis and Gastric Ulcer", Reports of Biochemistry & Molecular Biology, vol. 8, Oct. 2019, pp. 269-277.
Shohreh Azadi et al., "Upregulation of PD-L1 expression in breast cancer cells through the formation of 3D multicellular cancer aggregates under different chemical and mechanical conditions", Biochimica et Biophysica Acta (BBA)—Molecular Cell Research, vol. 1866, Issue 12, Dec. 2019, 118526.
Wu Z et al., "Claudin-7 (CLDN7) is overexpressed in gastric cancer and promotes gastric cancer cell proliferation, Invasion and maintains mesenchymal state", Neoplasma, Mar. 1, 2018, 65(3):349-359.
Hong-Fang Chen et al., "Protocadherin 7 inhibits cell migration and invasion through E-cadherin in gastric cancer", Tumor Biology, Apr. 2017: 1-11.
Naohiro Uraoka et al., "NRD1, which encodes nardilysin protein, promotes esophageal cancer cell invasion through Induction of MMP2 and MMP3 expression", Cancer Science, Jan. 2014;105(1):134-40. doi: 10.1111/cas.12316. Epub Nov. 29, 2013.
Valerie Stock et al., "Uptake and effects of orally ingested polystyrene microplastic particles in vitro and in vivo", Arch Toxicol. Jul. 2019;93(7):1817-1833. doi: 10.1007/s00204-019-02478-7. Epub May 28, 2019.

(Continued)

*Primary Examiner* — Sean E Aeder
(74) *Attorney, Agent, or Firm* — Revolution IP, PLLC

(57) ABSTRACT

The present invention relates to a biomarker composition for predicting the prognosis of cancer malignancy induced by exposure to microplastics and use thereof, and more particularly, it was confirmed that the expression level of CD44, E-cadherin, N-cadherin, PD-L1, NPAS2, NR1D1, DNMT1, SLC7A2, PCDH7 and CLDN7 was changed in cancer cell lines and animal models treated with polystyrene microspheres which are the one type of microplastic for 4 weeks, and malignancy was induced due to an increase in proliferation, migration and invasion of cancer cells by the change in the expression level of the gene, and 5-year overall survival rates in gastric cancer patients decreased and thus the genes may be provided as a biomarker composition for predicting the prognosis of cancer malignancies by exposure to microplastics.

2 Claims, 32 Drawing Sheets
Specification includes a Sequence Listing.

(56) References Cited

OTHER PUBLICATIONS

Yongfeng Deng et al., "Tissue accumulation of microplastics in mice and biomarker responses suggest widespread health risks of exposure", Scientific Reports | 7:46687 | DOI: 10.1038/srep46687.
Maurizio Forte et al., "Polystyrene nanoparticles internalization in human gastric adenocarcinoma cells", Toxicol In Vitro. Mar. 2016;31:126-36. doi: 10.1016/j.tiv.2015.11.006. Epub Nov. 14, 2015.
Roman Lehner et al., "Emergence of Nanoplastic in the Environment and Possible Impact on Human Health", Environmental Science & Technology 53(4): 1748-1765, 2019.
Tasuku Matsuoka et al., "Biomarkers of gastric cancer: Current topics and future perspective", World J Gastroenterol. Jul. 14, 2018; 24(26): 2818-2832.
Yang, Jingjing et al., "Research progress on the sources and toxicology of micro (nano) plastics in environment", Environmental Chemistry, vol. 37, No. 3, Mar. 2018, pp. 383-396.
Li, Cai-yan et al., "Molecular markers for prognosis of gastric cancer", J Int Oncol, Jun. 2013, vol. 40, No. 6, pp. 456-459.
Wang Zheng et al., "The expression and Significance of CD44 and SOX-2 in Gastric Carcinoma", Journal of Changzhi medical college, vol. 32, No. 2, Apr. 2018, pp. 85-88.

\* cited by examiner

BIOMARKER COMPOSITION FOR PREDICTING CANCER MALIGNANT PROGNOSIS INDUCED BY MICROPLASTIC EXPOSURE

CROSS-REFERENCE TO RELATED APPLICATION

This application claims priority to and the benefit of Korean Patent Application No. 10-2020-0038278 filed in the Korean Intellectual Property Office on Mar. 30, 2020, the entire contents of which are incorporated herein by reference.

SEQUENCE LISTING

This application contains a Sequence Listing submitted via EFS-Web and hereby incorporated by reference in its entirety. The Sequence Listing is named SEQCRF_2280-344.txt, created on May 31, 2021, and 3,038 bytes in size.

BACKGROUND OF THE DISCLOSURE

1. Field of the Disclosure

The present invention relates to a biomarker composition for predicting the prognosis of cancer malignancy induced by the exposure to microplastics and a use thereof.

2. Description of the Related Art

Gastric cancer is a very common cancer in Asia and is one of the leading causes of cancer deaths worldwide. In the past few years, many attempts have been made to better elucidate the biological processes involved in the development of gastric cancer, in order to improve understanding of the cancer mechanisms, as well as the early diagnosis and treatment of gastric cancer, but the molecular mechanisms involved in carcinogenesis of gastric cancer still remain the subject of intensive research.

In Korea, gastric cancer is the most frequent among all cancers, and the second most common cause of death. The stage of gastric cancer is determined by the degree of invasion of the surrounding area of the tumor, the metastasis to lymph nodes and metastasis to other organs, and accordingly, treatment and prognosis depend thereon. As the stage progresses, the prognosis gradually worsens, and especially the prognosis in the terminal stage (Stage 4) is so poor that the 5-year survival rate is only 3%.

Plastics have contributed greatly to the abundant daily life of modern people and industrial development due to their excellent functions and low prices, and recently, discarded plastics has been reported to decompose into microscopic sizes that are difficult to visually identify over time, thereby polluting the environment and threatening human health, but the effect of microplastics on cancer disease has not been studied.

PRIOR TECHNICAL LITERATURE

Patent Literature

Korean Patent Publication No. 10-2013-0109600 (published on Oct. 8, 2013)

SUMMARY OF THE DISCLOSURE

An object of the present invention is to provide a biomarker composition for predicting the prognosis of cancer malignancy induced by the exposure to microplastics and a method of providing information for predicting the prognosis of cancer malignancy using the same.

The present invention provides a biomarker composition for predicting prognosis of cancer malignancy induced by exposure to microplastics, comprising at least one protein selected from the group consisting of CD44, E-cadherin, N-cadherin, PD-L1 (programmed death-ligand 1), NPAS2 (Neuronal PAS domain protein 2), NR1 D1 (nuclear receptor subfamily 1 group D member 1), DNMT1 (DNA (cytosine-5)-methyltransferase 1), SLC7A2 (Solute Carrier Family 7 Member 2), PCDH7 (Protocadherin-7) and CLDN7 (Claudin 7).

The present invention provides a diagnostic kit for predicting prognosis of cancer malignancy induced by exposure to microplastics comprising at least one protein selected from the group consisting of CD44, E-cadherin, N-cadherin, PD-L1, NPAS2, NR1D1, DNMT1, SLC7A2, PCDH7 and CLDN7, and an agent for detecting expression or activity level of the protein, or expression level of gene encoding the protein as an active ingredient.

In addition, the present invention provides a method of providing information for predicting prognosis of cancer malignancy induced by exposure to microplastics comprising detecting expression or activity level of at least one protein selected from the group consisting of CD44, E-cadherin, N-cadherin, PD-L1, NPAS2, NR1D1, DNMT1, SLC7A2, PCDH7 and CLDN7, or expression level of gene encoding the protein in a sample isolated from specimen.

DETAILED DESCRIPTION OF THE EMBODIMENTS

Figure 1A:
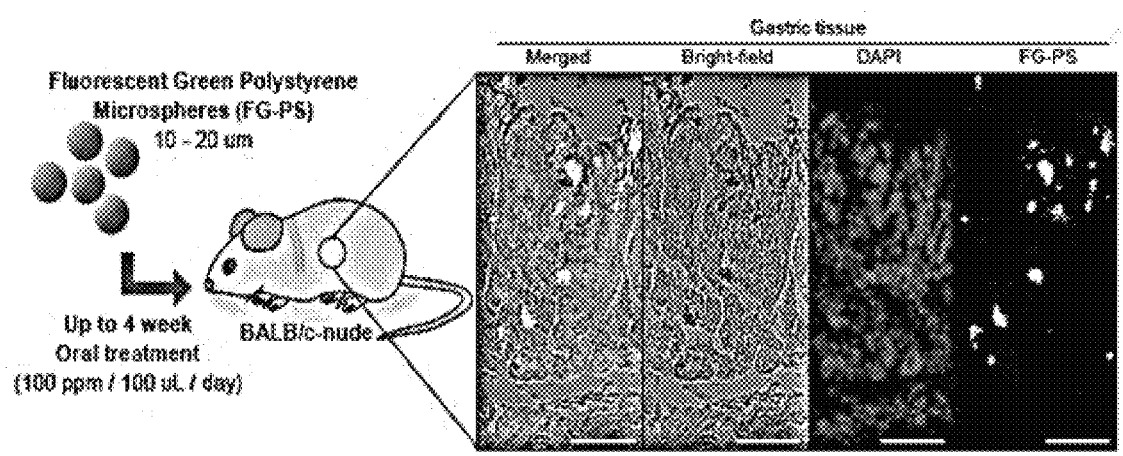
FIG. 1A is the representative microscopy images showing accumulation of fluorescent green polyethylene in gastric tissue (magnification: 20×, scale bar, 100 µm)
Figure 1B:
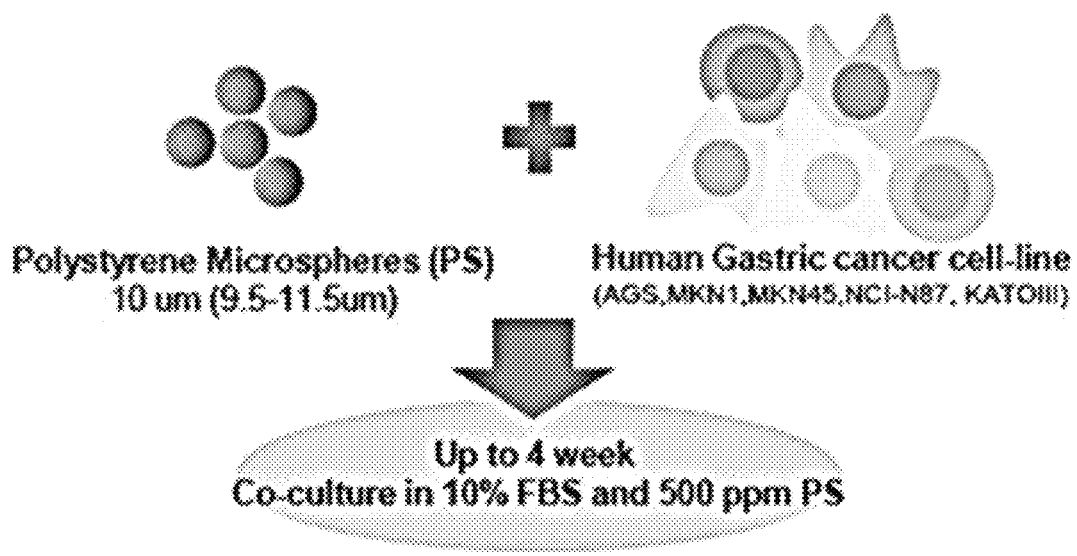
FIG. 1B shows a result of cultured cells exposed to 500 ppm of polystyrene (PS) (10 µm diameter) for 4 weeks.
Figure 1C:
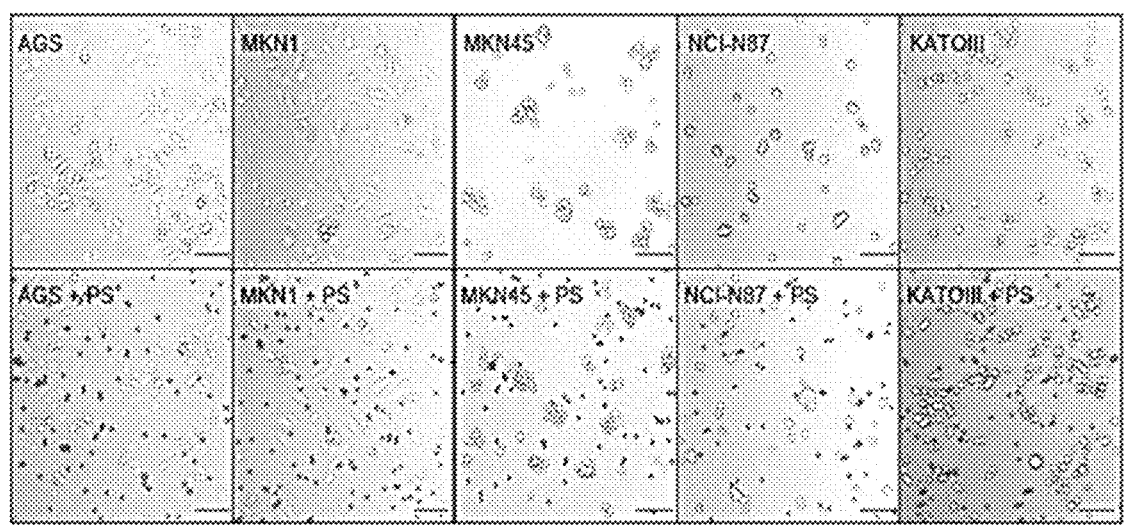
FIG. 1C shows microscopy images of AGS, MKN1, MKN45, NCI-N87, and KATO Ill cells with/without PS exposure (Magnification: 20×, scale bar, 100 µm.)

Hereinafter, the present invention will be described in more detail.

As microplastics with diameters less than 5 mm are being recognized as a new environmental treat and human health risk, the present inventors investigated the effects of the microplastic polystyrene (PS) on the hallmarks of cancer changes and 5-year overall survival (OS) to study the risks that may occur when PS, a type of microplastic, are ingested in vivo and as a result, they confirmed that when PS is ingested in vivo, the gastric cancer was exacerbated through the change in the expression level of the gene in the stomach tissue, which is the primary site of exposure and completed the present invention.

In the present invention, the present invention is at least one protein selected from the group consisting of CD44, E-cadherin, N-cadherin, PD-1, NPAS2, NR1D1, DNMT1, SLC7A2, PCDH7 and CLDN7, and it is possible to provide a biomarker composition for predicting prognosis of cancer malignancy induced by exposure to microplastics.

In more detail, the biomarker composition may be one or two or more selected from the group consisting of CD44 (NCBI No. 960), E-cadherin (NCBI No. 999), N-cadherin (NCBI No. 1000), PD-L1 (programmed death-ligand 1, NCBI No. 29126), NPAS2 (Neuronal PAS domain protein 2, NCBI No. 4862), NR1D1 (nuclear receptor subfamily 1 group D member 1, NCBI No. 9572), DNMT1 (DNA (cytosine-5)-methyltransferase 1, NCBI No. 1786), SLC7A2 (Solute Carrier Family 7 Member 2, NCBI No. 6542), PCDH7 (Protocadherin-7, NCBI No. 5099) and CLDN7 (Claudin 7, NCBI No. 1366).

The microplastics may be selected from the group consisting of polystyrene, polypropylene, polyethylene, polyamide (PA), acrylonitrile-butadiene-styrene (ABS), polytetrafluoroethylene (PTFE), cellulose acetate (CA), polycarbonate (PC), polymethyl methacrylate (PMMA), polyvinyl chloride (PVC) and polyethylene terephthalate (PET).

The CD44, N-cadherin, PD-L1, NR1D1, SLC7A2 and PCDH7 may increase in the expression in cancer cells exposed to the microplastics.

The E-cadherin, NPAS2, DNMT1 and CLDN7 may reduce in the expression in cancer cells exposed to the microplastics.

The cancer may be selected from the group consisting of gastric cancer, breast cancer, uterine cancer, liver cancer, colon cancer, kidney cancer, lung cancer, prostate cancer, oral cancer and pancreatic cancer.

The present invention may provide a diagnostic kit for predicting prognosis of cancer malignancy induced by exposure to microplastics comprising at least one protein selected from the group consisting of CD44, E-cadherin, N-cadherin, PD-L1, NPAS2, NR1D1, DNMT1, SLC7A2, PCDH7 and is CLDN7, and an agent for detecting expression or activity level of the protein, or expression level of gene encoding the protein as an active ingredient.

The agent may be selected from the group consisting of primers, probes, antibodies, peptides and aptamers.

In addition, the present invention may provide a method of providing information for predicting prognosis of cancer malignancy induced by exposure to microplastics comprising detecting expression or activity level of at least one protein selected from the group consisting of CD44, E-cadherin, N-cadherin, PD-L1, NPAS2, NR1D1, DNMT1, SLC7A2, PCDH7 and CLDN7, or expression level of gene encoding the protein in a sample isolated from specimen.

As used herein, "biomarker" refers to a substance capable of diagnosing a tissue or cell of a subject with gastric cancer by distinguishing it from a tissue or cell of a normal control group and includes organic biomolecules such as proteins, nucleic acids, lipids, glycolipids, glycoproteins, and the like, which show an increase or decrease in tissues or cells of a diseased object compared to the normal control group.

As used herein, "prognosis" includes determining whether an object for a specific disease or symptom, that is, the subject to be tested will have the autologous disease in the future, or determining the responsiveness of the subject to be tested to the treatment.

Hereinafter, the present invention will be described in more detail through examples. These examples are only intended to illustrate the present invention in more detail, and it will be apparent to those skilled in the art that the scope of the present invention is not limited by these examples according to the gist of the present invention.

The following experimental examples are intended to provide experimental examples commonly applied to each of the examples according to the present invention.

Experimental Example

1. Animal Model for Microplastic Accumulation in Gastric Tissue

To identify the microplastic accumulation in gastric tissue, fluorescent green polyethylene microspheres (100 ppm/100 μL; 10-20 μm; Cospheric, USA) was used. Fluorescent green polyethylene microspheres were orally administered to 5-week-old BALB/c nude mice daily for 4 weeks.

After 4 weeks, mice were euthanized using $CO_2$. The stomach was isolated and fixed overnight with 4% PFA at 4° C.

Frozen slides (8 μm thick) were generated using optimal cutting temperature (OCT) compound, and the slides were attached to slide glass. Cell nuclei were stained with DAPI (ThermoFisher Scientific, USA), and images were obtained using an IN cell analyzer 2200 (GE Healthcare, USA)

2. Polystyrene Microspheres (PS)

To identify the effect of microplastic to gastric cancer cells, polystyrene microspheres (PS) (500 mg, 9.5-11.5 μm, Cospheric, USA) was used. PS were mixed with 10 mL of normal RPMI culture medium containing 10% FBS and 1% antibiotics.

Ultrasonic grinding and vortexing were repeatedly performed to create a 5% PS suspension, which was then aliquoted to cell culture media to the desired concentration during subculture.

The PS was removed by washing three times with PBS. EDTA-trypsin was used during subculture.

3. Cell Culture

The human gastric cancer cell lines, AGS, MKN1, MKN45, KATO III, were obtained from the Korea Cell-Line Bank (KLCB, Korea). NCI-N87 was obtained from the American Type Culture Collection (ATCC, USA).

All cell lines maintained in RPMI 1640 medium (Corning, USA) supplemented with 10% fetal bovine serum (FBS) and 1% penicillin/streptomycin at 37° C. in 5% $CO_2$.

4. Invasion and Migration Assay

Cells ($1\times10^5$ cells per mL) were suspended in 0.2 mL of serum-free RPMI for invasion and motility assays.

For the invasion assay, the cells were loaded in the upper well of the Transwell chamber (8-um pore size; SPL, Korea) that was pre-coated with Matrigel (Corning, USA) on an upper side of the chamber; the lower well was filled with 0.75 mL of RPMI with 20% serum.

After incubation for 48 h at 37° C., non-invaded cells on the upper surface of the filter were removed with a cotton swab, and migrated cells on the lower surface of the filter were fixed and stained with a Crystal violet menthol solution (Sigma-Aldrich, USA) and photographed at ×20 magnification.

Invasiveness was determined by counting cells in four microscopic fields per well, and the extent of invasion was expressed as an average number of cells per microscopic field.

For migration studies, we used invasion chambers with control inserts that contained Matrigel. Cells ($5\times10^4$ cells per mL) in 0.2 mL of serum-free RPMI were added to the apical side of each insert, and 0.75 mL of RPMI with 20% serum was added to the basal side of each insert. The inserts were processed as described above for the invasion assay.

5. Flow Cytometry

To detect N-cadherin, CD44, and PD-L1 expression, cells were exposed to PS for 4 weeks, dislodged with EDTA-trypsin, and then collected in 5-mL FACS tubes ($1\times10^6$ cells/tube).

Cells were centrifuged, the supernatant was aspirated, and 4% paraformaldehyde was added and allowed to incubate for 30 min at room temperature. After removing the fixation buffer, permeabilization buffer (0.02% Triton-X in distilled water) was added to the cells.

After removing the buffer, cells were incubated with blocking buffer containing 1% BSA with 10% normal goat serum for 1 h at room temperature. Cells were then incubated with primary antibody (anti-N-cadherin, anti-CD44, or anti-PD-L1 antibody) overnight at 4° C. After washing 3 times by PBS, cells were incubated with Alexa Fluor-647 goat anti-rabbit IgG (H+L) at room temperature in the dark for 60 min.

After, washing 3 times by PBS, antibody signals were detected by flow cytometry (BD Accuri™ C6 Plus, Becton Dickinson Biosciences, USA).

6. Immunocytochemistry (ICC)

Briefly, cells were seeded onto a 2-well chamber slide (Falcon, USA) with RPMI 1640 medium (Corning, USA) supplemented with 10% FBS at a density of $1\times10^5$ cells/mL and treated with PS at 500 ppm.

Cells were incubated overnight at 37° C. in 5% $CO_2$, the culture medium was removed, and cells were washed 3 times with PBS and fixed with 4% paraformaldehyde for 20 min at room temperature.

After fixation, the samples were permeabilized by incubation with 0.02% Triton-X in distilled water for 20 min at room temperature. After the buffer was removed, cells were incubated with blocking buffer (1% BSA and 10% normal goat serum) for 1 h at room temperature and cells were incubated with primary antibody overnight at 4° C.

N-cadherin and E-cadherin were detected with Alexa Fluor-488 goat anti-rabbit IgG (H+L) and Alexa Fluor-647 goat anti-mouse IgG (H+L), respectively. PD-L1 was detected with Alexa Fluor-647 goat anti-rabbit IgG (H+L), and CD44 was detected with Alexa Fluor-488 goat anti-mouse IgG (H+L).

The slides were treated with DAPI and analyzed by confocal microscopy (LSM-710, Zeiss, Germany).

7. Quantitative Real-Time PCR (qPCR)

Total RNA was extracted from cells using TRIzol (Molecular Research Center, USA) in accordance with the manufacturer's instructions.

RNA was quantified by spectrophotometry and then diluted in RNase-free $dH_2O$ (ThermoFisher Scientific, USA).

For the PCR reaction, a SuperScript III cDNA Synthesis Kit (Invitrogen, USA) was used to generate cDNA from 5 μg of mRNA following the manufacturer's instructions.

qPCR was performed on an ABI PCR system (Applied Biosystems, USA) using SYBR Green PCR Master Mix (Applied Biosystems, USA) following the manufacturer's instructions. The reaction conditions were: 10 min at 95° C. followed by 50 cycles of 95° C. for 15 s, 60° C. for 60 s.

The primer sequences are described in Supplementary Table 1. mRNA values were normalized to GAPDH, relative quantity values of mRNA (RQ value) were calculated with the following equation:

$$RQ = 2^{-\Delta\Delta C_t}$$

TABLE 1

Primers

| Target | | Sequence | |
|---|---|---|---|
| GAPDH | Forward | GCCTCAAGATCATCAGCAATGCCT (SEQ ID NO: 1) | N.A |
| | Reverse | TGTGGTCATGAGTCCTTCCACGAT (SEQ ID NO: 2) | N.A |
| N-cadherin | Forward | AGAGGCTTCTGGTGAAATCGC (SEQ ID NO: 3) | N.A |
| | Reverse | TGGAAAGCTTCTCACGGCAT (SEQ ID NO: 4) | N.A |
| CD44 | Forward | CCAATGCCTTTGATGGACC (SEQ ID NO: 5) | N.A |
| | Reverse | TCTGTCTGTGCTGTCGGTGAT (SEQ ID NO: 6) | N.A |
| PD-L1 | Forward | TTGGGAAATGGAGGATAAGA (SEQ ID NO: 7) | N.A |
| | Reverse | GGATGTGCCAGAGGTAGTTCT (SEQ ID NO: 8) | N.A |
| NR1D1 | Forward | CTGGACTCCAACAACAACACAG (SEQ ID NO: 9) | N.A |
| | Reverse | GGGGATGGTGGGAAGTAGGT (SEQ ID NO: 10) | N.A |
| NPAS2 | Forward | GTATCACGCCTCTCCTTGGG (SEQ ID NO: 11) | N.A |
| | Reverse | ATTACAGGAGGGCTAGGCA (SEQ ID NO: 12) | N.A |
| ACE2 | Forward | CATTGGAGCAAGTGTTGGATCTT (SEQ ID NO: 13) | N.A |
| | Reverse | GAGCTAATGCATGCCATTCTCA (SEQ ID NO: 14) | N.A |

8. Western Blot

Cell extracts were obtained using Extraction Cell Lysis Buffer 1× (Abcam, UK) containing Extraction Enhancer Buffer (Abcam, UK), and protein concentration was determined by BCA assay (ThermoFisher Scientific, USA).

Western blot analysis was performed using the antibodies listed in Table 2.

TABLE 2

| Material or Reagent | Source | Cat. No. |
|---|---|---|
| Antibody | | |
| N-cadherin | Abcam, UK, | ab76057(for ICC, Flow cytometer) ab76011 (for WB) |
| E-cadherin | Abcam, UK, | ab1416 |
| CD44 | Abcam, UK, | ab1416 (for ICC/IF, Flow cytometer) ab157107 (for WB) |
| PD-L1 | Abcam, UK, | ab205921 |
| DNMT1 | Abcam, UK, | ab134148 |
| AGTR1 | Abcam, UK, | ab124734 |
| Beta Actin | Abcam, UK, | ab6276 |
| Anti-Rabbit/-Mouse-HRP | Abcam, UK, | ab205718ab205719 |
| Anti-Rabbit/Mouse-Alexa488 | Abcam, UK, | ab150077ab150113 |
| Anti-Rabbit/Mouse-Alexa647 | Abcam, UK, | ab150079ab150115 |

9. Cytotoxicity

To investigate PS cytotoxicity, cell proliferation was measured by the alamarBlue® assay (ThermoFisher Scientific, USA) following the manufacturer's instructions.

Briefly, cells were seeded onto 96-well culture plates with RPMI-1640 medium supplemented with 10% FBS at a density of 5000 cells/well and treated PS microspheres.

Cell viability was measured at $\lambda ex=560$ nm and $\lambda em=590$ nm using a microplate reader (i3X, Molecular Devices, USA).

The emission values are stated as percentages of controls, yielding the percent cell proliferation after 72 h of seeding the plate.

10. Assessment of Drug Resistance

To assess the drug resistance due to CD44, cytotoxicity was measured using bortezomib or cisplatin. Cytotoxicity was determined by the alamarBlue® assay (Thermo Fisher Scientific, Waltham, MA) following the manufacturer's instructions.

Briefly, Cells were exposed to PS for 4 weeks, collected in tube. After, cells were seeded onto 96-well culture plates with medium supplemented with 10% FBS at a density of $1 \times 10^5$ cells/mL concertation with 500 ppm PS.

After overnights, removed culture media and treated with Bortezomib (Takeda Oncology, USA, 10 nM in PBS), or Cisplatin (United states Pharmacopeia, USA, 1.5 ug/mL in DMSO) with RPMI-1640 medium supplemented with 5% FBS and/or PS 500 ppm.

Cytotoxicity was measured at an emission of 590 nm using a microplate reader.

The emission values are stated as percentages of vehicle controls, yielding percentage cell viability after 72 h of treatment.

Then, Δcytotoxicity was calculated as followings:

Δ cytotoxicity=cytotoxicity with PS—cytotoxicity without PS

11. RNAseq

To confirm changes in gene expression in gastric tissues due to PS exposure, mice were orally administered 10-μm PS microspheres (100 ppm/100 μL PBS) for 4 weeks.

Total RNA was extracted from the stomach tissues.

The RNA was randomly fragmented for sequencing with short reads, which were then reverse transcribed to cDNA with different adapters attached to the 5' and 3' ends.

PCR amplification was performed to the extent that sequencing was possible, and size selection was performed to obtain an insert size of 200-400 bp, which was used for NovaSeq 6000 Sequencing System (illumina, USA) with the manufacturer's instructions.

The expression profile was extracted with FPKM (Fragments Per Kilobase of transcript per Million mapped reads), which is a normalization value that accounts for read count, transcript length, and depth of coverage.

12. Data Analysis of TCGA—STAD

Overall survival analysis was performed using The Human Protein ATLAS web toolkit (https://www.proteinatlas.org/) using the RNAseq data from 354 patients in The Cancer Genome Atlas-Stomach Adenocarcinoma (TCGA-STAD) dataset.

The demographic data was listed in Table 3.

Based on the FPKM value of each gene, patients were classified into two expression groups (high and low), and the correlation between expression level and patient survival was examined.

To classify the two expression categories, the best expression cutoff value in the Protein ATLAS web-toolkit was used. The prognosis of each group of patients was examined by Kaplan-Meier survival estimators, and the survival outcome of the two groups were compared by log-rank test.

The overall survival (OS) results included all Stage I-IV and N/A patients. FPKM values above 1, which was recommended by The Human Protein ATLAS, and p<0.0001, indicated a significant OS.

TABLE 3

| Variables | Counts (n= 354) | |
|---|---|---|
| Age( years) | | |
| ≤60 | 241 | 68.1% |
| >60 | 107 | 30.2% |
| N/A | 6 | 1.7% |
| Gender | | |
| Female | 125 | 35.3% |
| Male | 229 | 64.7% |
| Pathologic stage | | |
| Stage I | 48 | 13.6% |
| Stage II | 110 | 31.1% |
| Stage III | 146 | 41.2% |
| Stage IV | 35 | 9.9% |
| N/A | 15 | 4.2% |

N/A: not available.

13. Cytoscape Network Analysis

Gene sets were downloaded from the MSigDB database of the Broad Institute (http://software/broadinstitute.org/gsea/msigdb), and hallmark gene signature (H) sets and oncogene signatures (C6) gene sets were selected to perform quantification of RNAseq gene lists (Fold change>2, p<0.05).

All top-ranked gene sets were manually curated to confirm their accurate functional and pathway categorizations (p<0.05, top 20).

The interaction network was analyzed with STRING software.

Briefly, Cytocape String App (Version 1.4.0) were downloaded from the official website. In this study, we selected significant RNAseq gene lists for network analysis (Fold change>2, p<0.05).

<Example> Confirmation of Effect of Microplastic Exposure on Gastric Cancer Onset and Malignancies Microplastics with diameters less than 5 mm are being recognized as a new environmental threat and human health risk. Polystyrene microspheres (PS) are the one type of microplastic. In vivo studies using mice reported that deposition of PS in the liver, kidney, and gut was observed after oral administration of PS particles sized 1-10 μm. Moreover, exposure of mice to PS led to disturbed intestinal microbiome However, it has not been revealed whether PS induce changes in cancer hallmarks and the effect of 5-year overall survival (OS). The stomach is the primary site of exposure when PS are ingested in vivo and given the deleterious effects of PS exposure, it was hypothesized that it may exacerbate gastric cancer.

The important hallmarks of cancer include cancer cell proliferation and metastasis, circadian clock, immunosuppressive environment, and expression of stem cell markers. This study aimed to evaluate the effects of PS on gastric cancer. To confirm accumulation of PS into the digestive tract, BALB/nude mice were fed daily with 100 ppm/100 μL of 10-20-μm sized fluorescent green polyethylene for 4 weeks.

Figure 2:
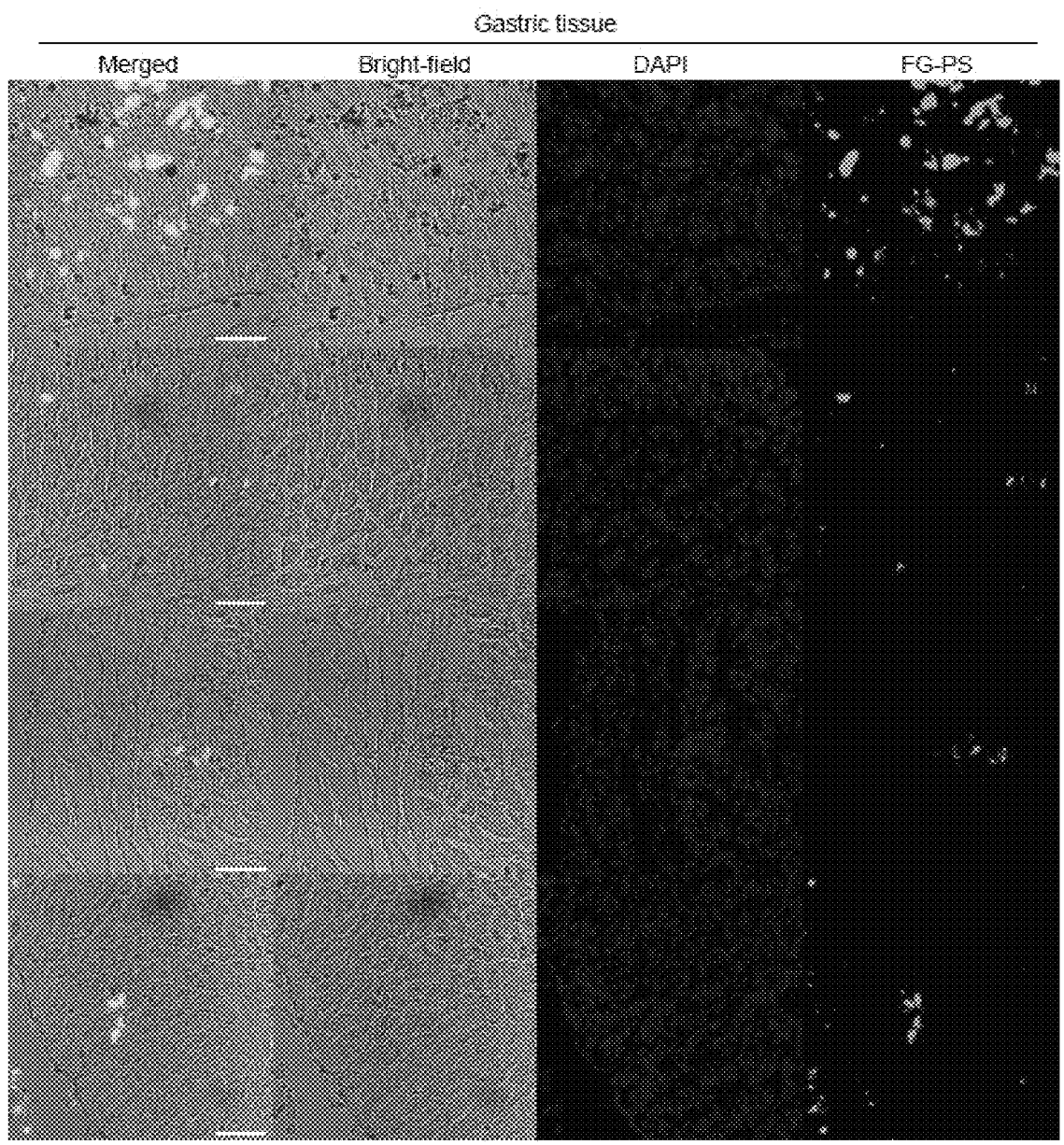
FIG. 2 shows the fluorescent green polyethylene (FG-PS) accumulation in gastric tissue. 100 ppm/100 µL of FG-PS was exposed to BALB/c nude mice were exposed for 4 weeks and after sacrifice of mice, the accumulation of FG-PS was imaged by confocal microscopy. FG-PS was deposited at gastric mucosal layers and sub-mucosal layers. FG-MS was indicated by red arrow in bright field image (magnification: 20×, scale bar, 100 µm).

Fluorescent green polyethylene signals were observed in the gastric tissue (FIG. 1A and FIG. 2).

Figure 1D:
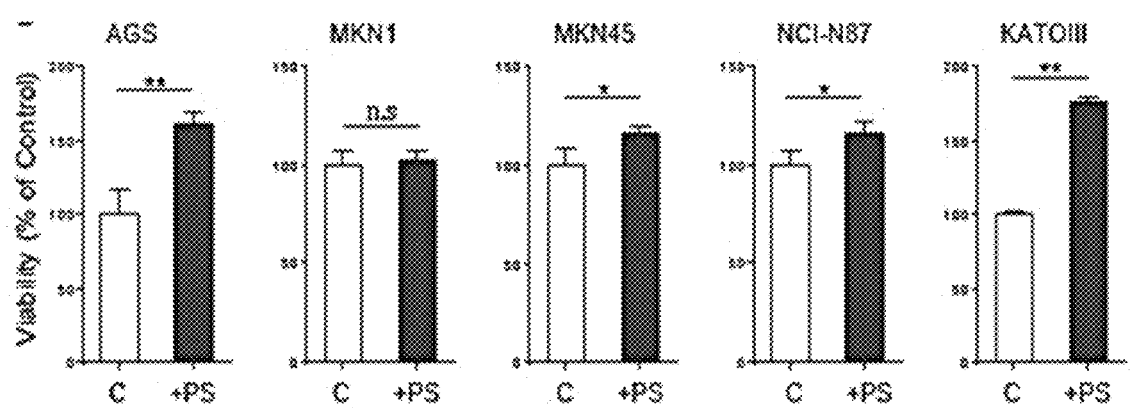
FIG. 1D shows PS exposure induced increased proliferation of AGS, MKN45, NCI-M87, and KATOIII compared to the control (mean±SD. *P<0.05, **P<0.005, n.s., not significant. student's t-test).

After confirming PS can directly interact with the stomach, PS was exposed to human gastric cancer cell lines (AGS, MKN1, MKN45, NCI-N87, and KATOIII) for 4 weeks. As a result, it was confirmed that increases of proliferation were observed (*P<0.05, **P<0.005) as shown in FIG. 1D.

Figure 3A:
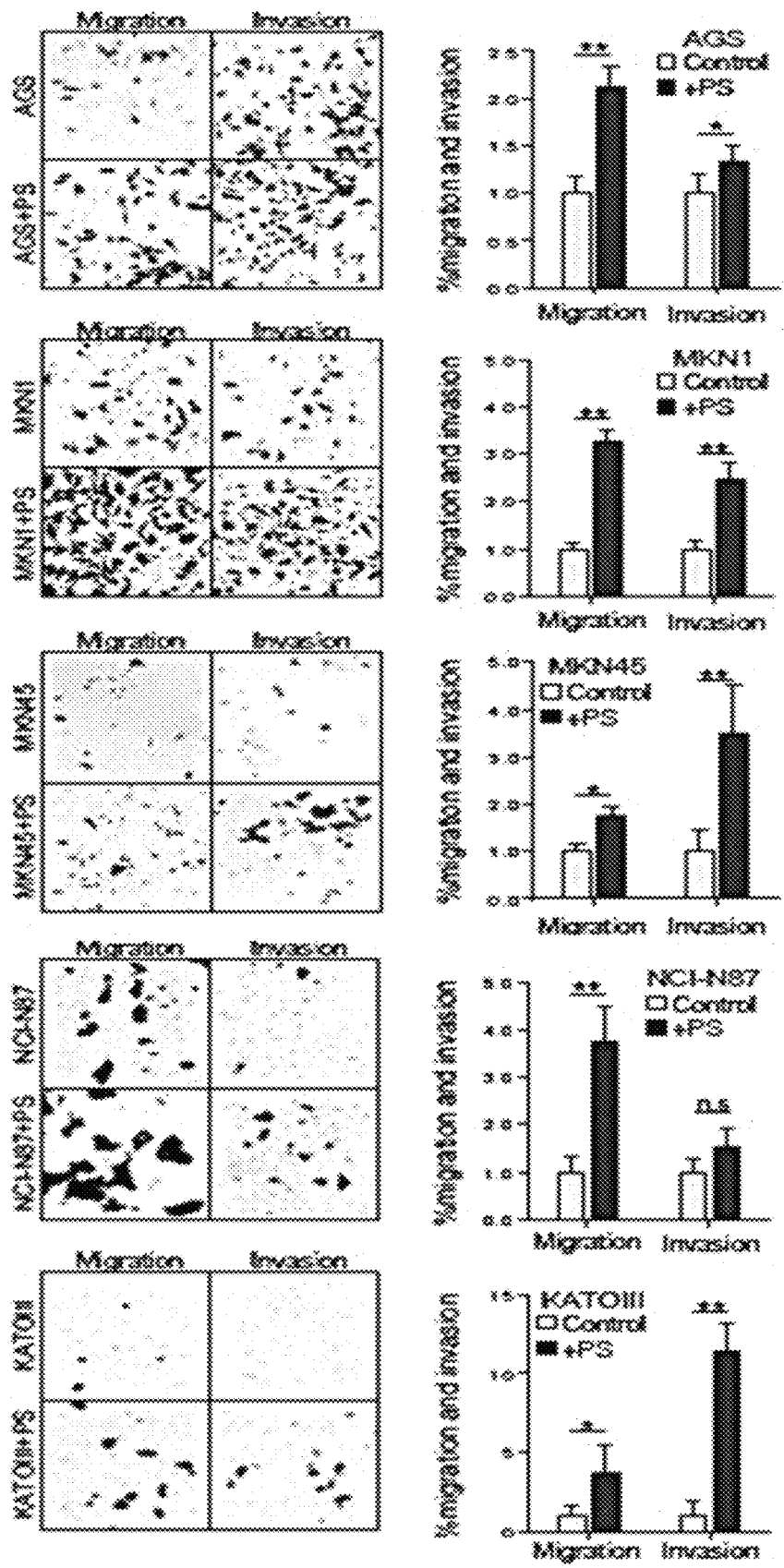
FIG. 3A shows in vitro migration and invasion assays and bar graphs represent the average number of cells on the underside of the membrane, normalized to the control condition. PS promoted invasion and migration of every gastric cancer cell (Magnification: 20×, mean±SD. *P<0.05, ** P<0.005, n.s., not significant. Student's t-test)

Next, to determine whether PS exposure induces changes in invasion, migration, and epithelial mesenchymal transition, the migration and invasion rates were measured As a result, it was confirmed that 2.12, 3.24, 1.74, 3.78, and 3.71-fold increases of migration rate were observed in AGS, MKN1, MKN45, NCI-N87, and KATOIII cells, respectively and invasion rates were elevated by 1.33, 2.47, 3.48, and 11.4-fold in AGS, MKN1, MKN45, and KATOIII cells, respectively (*P<0.05, **P<0.005) as shown in FIG. 3A.

Figure 3B:
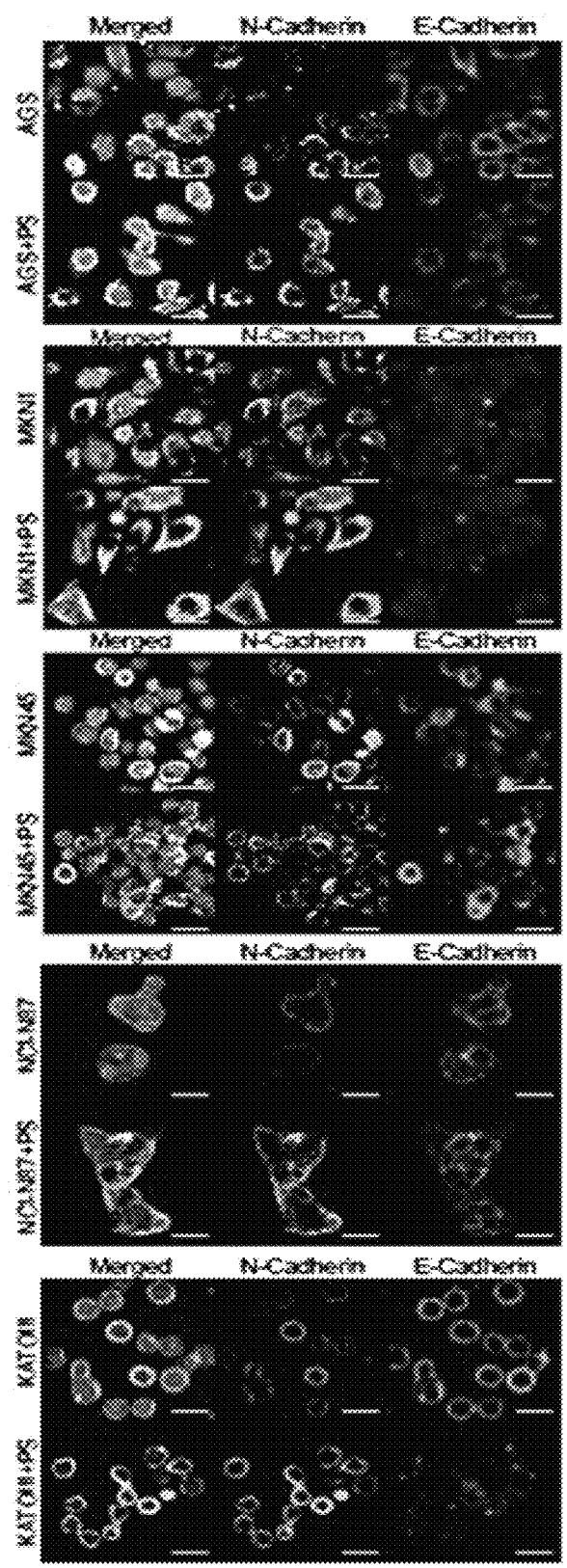
FIG. 3B shows immunocytochemistry images showing gastric cancer cells stained for E-cadherin and N-cadherin and PS exposure (10 µm diameter, 500 ppm, 4 weeks) decreased E-cadherin levels in AGS and KATOIII cells and increased N-cadherin levels in AGS, NCI-N87, and KATOIII cells (Magnification: 40×, Scale bar: 20 µm)
Figure 3C:
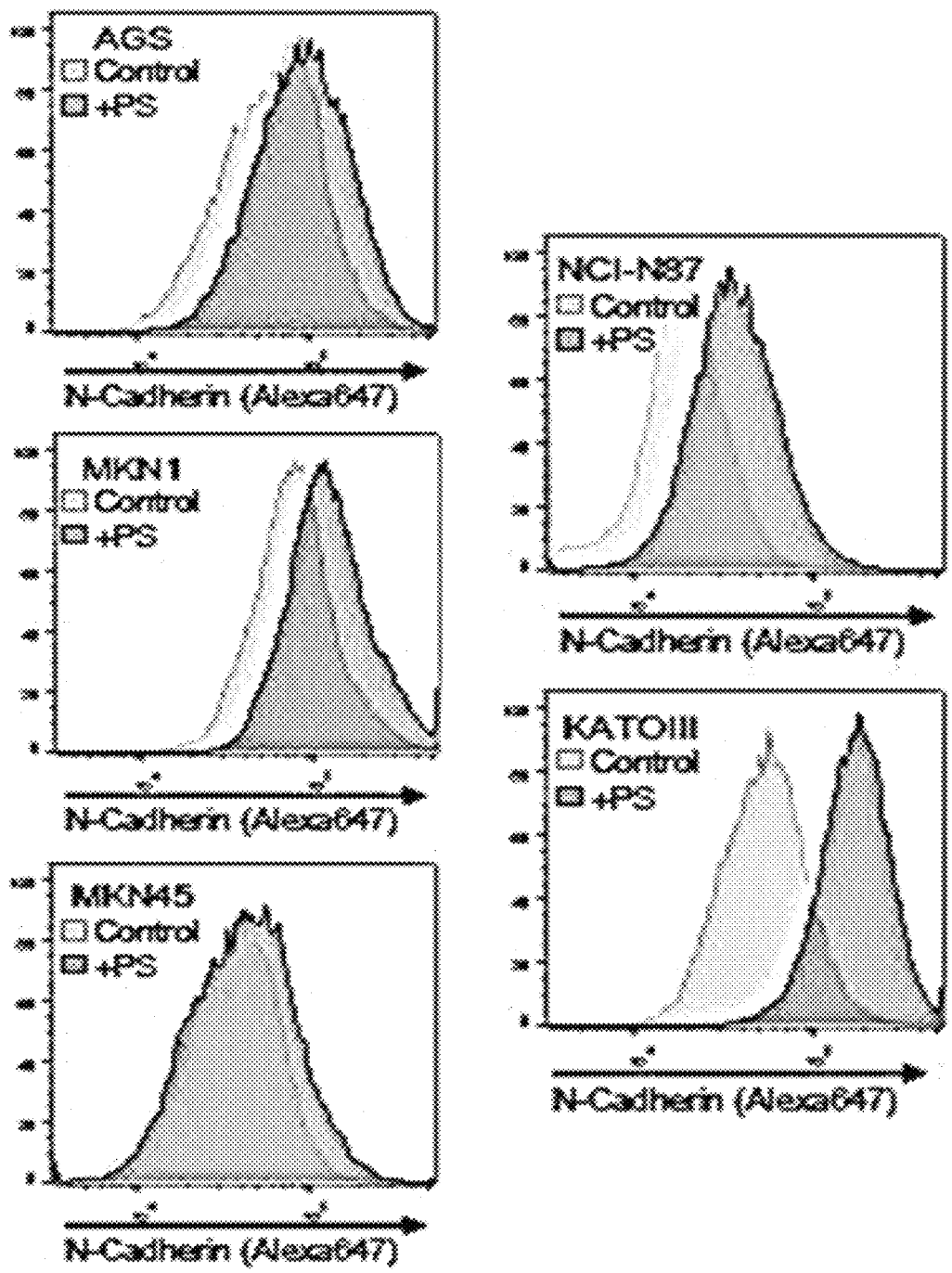
FIG. 3C shows flow cytometry histograms of N-cadherin expression in gastric cancer cell lines with/without PS exposure and PS exposure upregulates N-cadherin expression in gastric cancer cell after exposure to PS.

In addition, FIG. 3B shows immunohistochemistry results of N-cadherin and E-cadherin after PS exposure and in parallel to this result, flow cytometry experiments showed elevated levels of N-cadherin was 1.51, 1.59, 1.35, 2.05, 3.07-fold increases in AGS, MKN1, NCI-N87, and KATOIII cells (FIG. 3C).

Figure 3D:
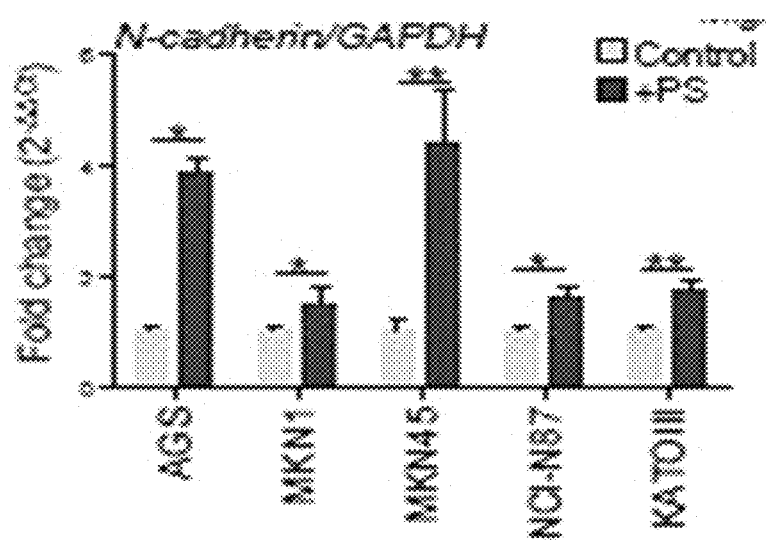
FIG. 3D shows qPCR analysis of N-cadherin mRNA expression. mRNA expression of N-cadherin increased after PS exposure (mean±SD, *P<0.05, ** P<0.005, Student's t-test)
Figure 3E:
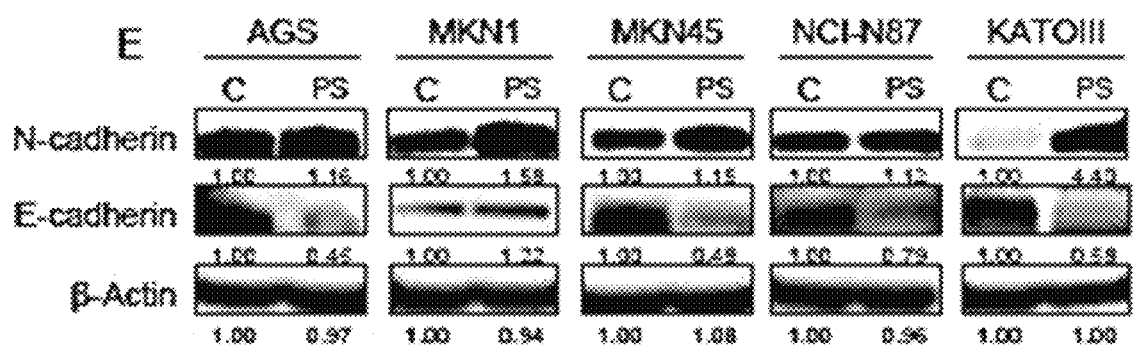
FIG. 3E shows western blot analysis of N-cadherin and E-cadherin expressions with/without PS.

Quantitatively, qPCR results showed 3.84, 1.47, 4.40, 1.61, and 1.71-fold increases of N-cadherin gene expression after PS exposure in AGS, MKN1, MKN45, NCI-N87 and KATOIII cells, respectively (FIG. 3D). Western blot results showed the decreased E-cadherin and increased N-cadherin following PS exposure except MKN1 cells (FIG. 3E).

Figure 4:
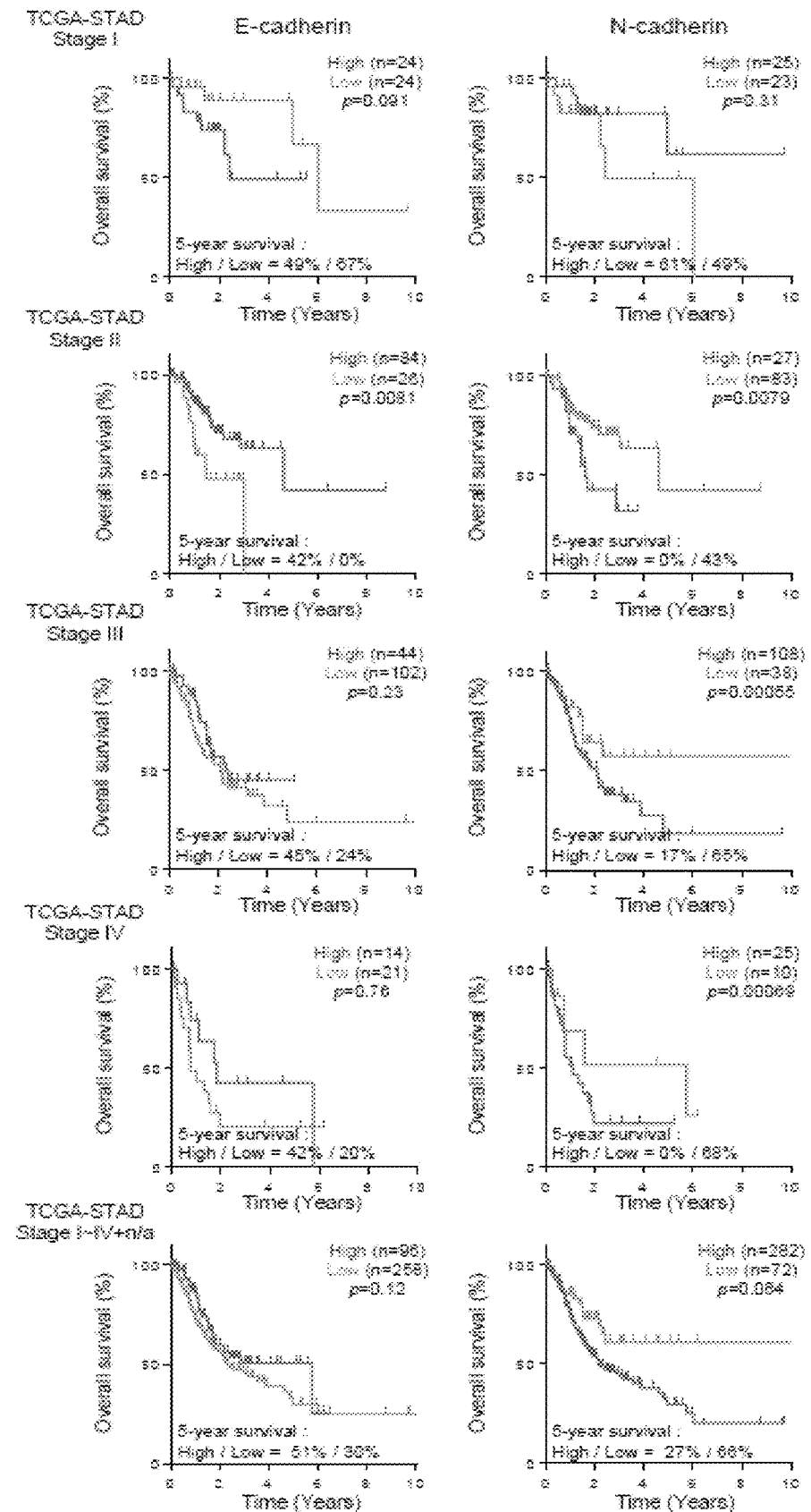
FIG. 4 shows 5-year overall survival (OS) rate of Cancer Genome Atlas Stomach Adenocarcinoma (TCGA-STAD) datasets. Kaplan-Meier plots showed 5-year OS was correlated with expression of E-cadherin and N-cadherin. The Cancer Genome Atlas Stomach Adenocarcinoma (TCGA-STAD) datasets identified that high N-cadherin expression showed poor 5-years overall survival rate (OS) in stage II (P=0.079), III (P=0.00055), IV (P=0.00069), and low E-cadherin expression showed poor 5-years OS in stage II (P=0.0081) (P-value: log rank t-test).

The correlated gene expression was investigated in Cancer Genome Atlas Stomach Adenocarcinoma (TCGA-STAD) datasets using finding of RNAseq in mouse model. In the TCGA-STAD datasets, it is confirmed that high N-cadherin expression showed poor 5-year overall survival rate (OS) in stage II (P=0.079), III (P 5=0.00055), IV (P=0.00069), and low E-cadherin expression showed poor 5-year OS in stage II (P=0.0081) as shown in FIG. 4.

Figure 5A:
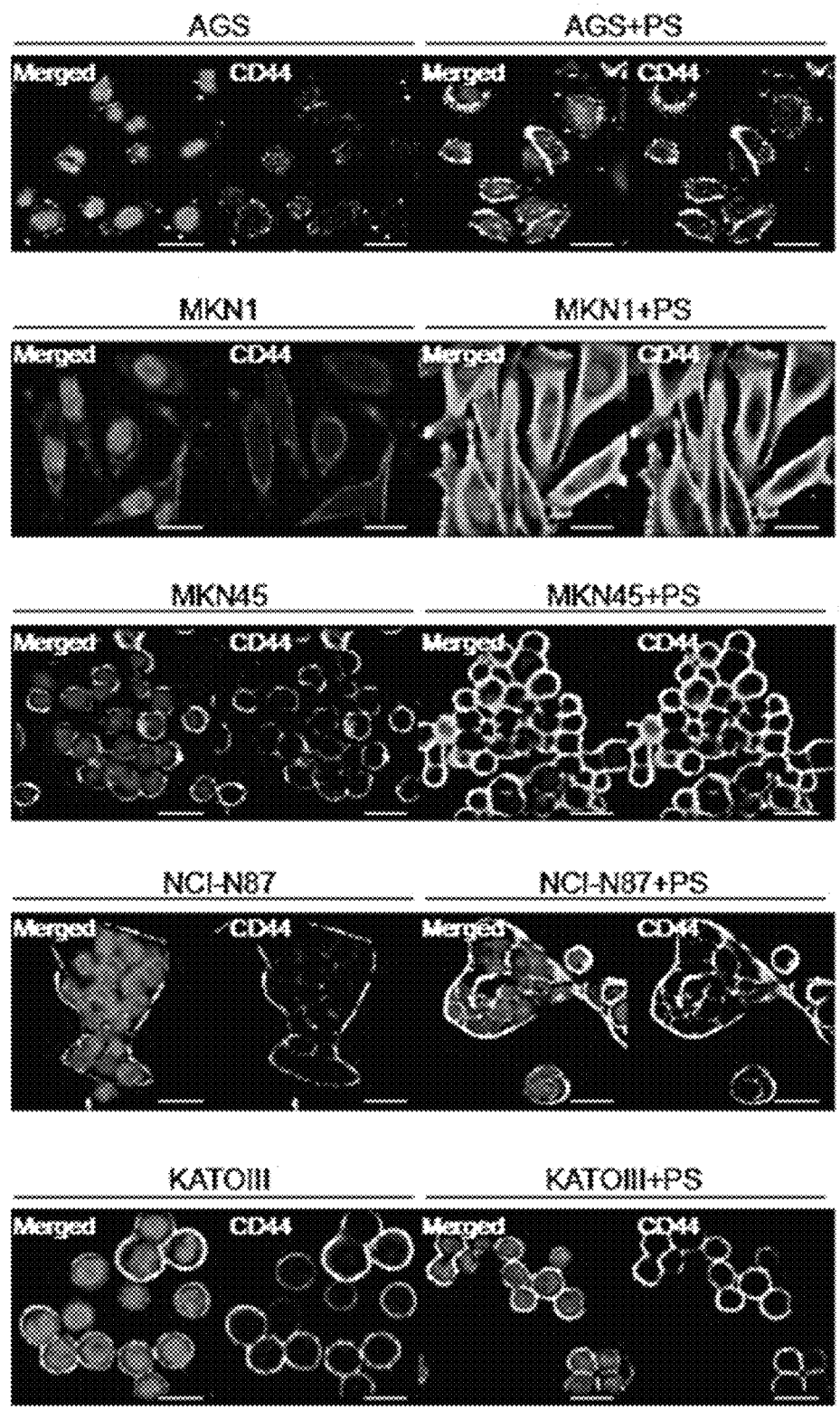
FIG. 5A shows CD44 expression in gastric cancer cells by immunofluorescence staining (magnification: 40×, scale bar: 20 μm)
Figure 5B:
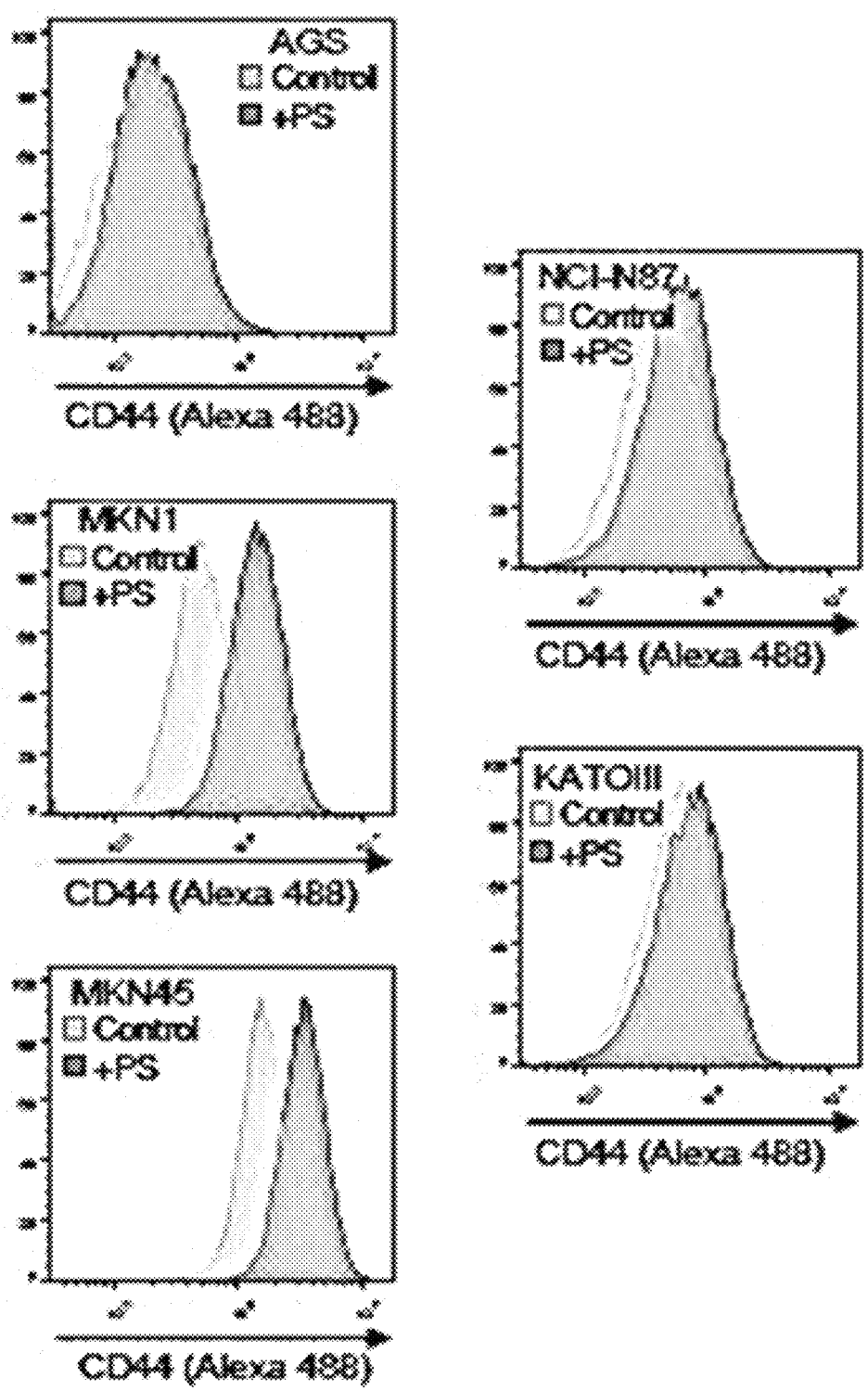
FIG. 5B shows flow cytometry analysis of CD44 expression in gastric cancer cell lines and PS exposure for 4 weeks increased CD44 expression.
Figure 5C:
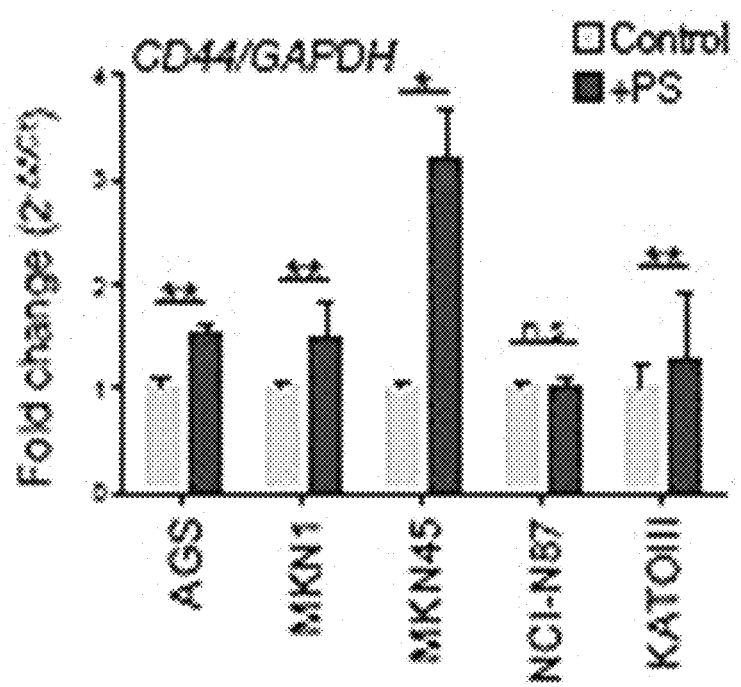
FIG. 5C shows qPCR analysis of CD44 mRNA expression (mean±SD, *P<0.05, **P<0.005, student's t-test n.s., not significant)
Figure 5D:
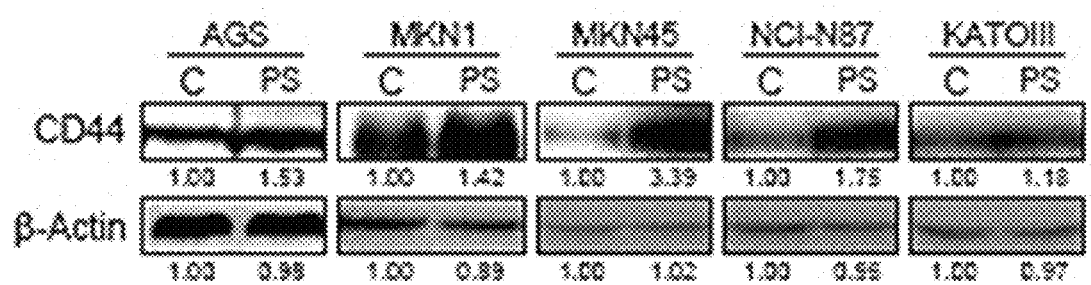
FIG. 5D shows western blotting analysis of CD44 expression in cells with/without PS.

Upregulated CD44 expression was found by immunohistochemistry (FIG. 5A). mRNA level and protein level of CD44 increased in five cell lines (FIG. 5B to FIG. 5D).

Figure 6A:
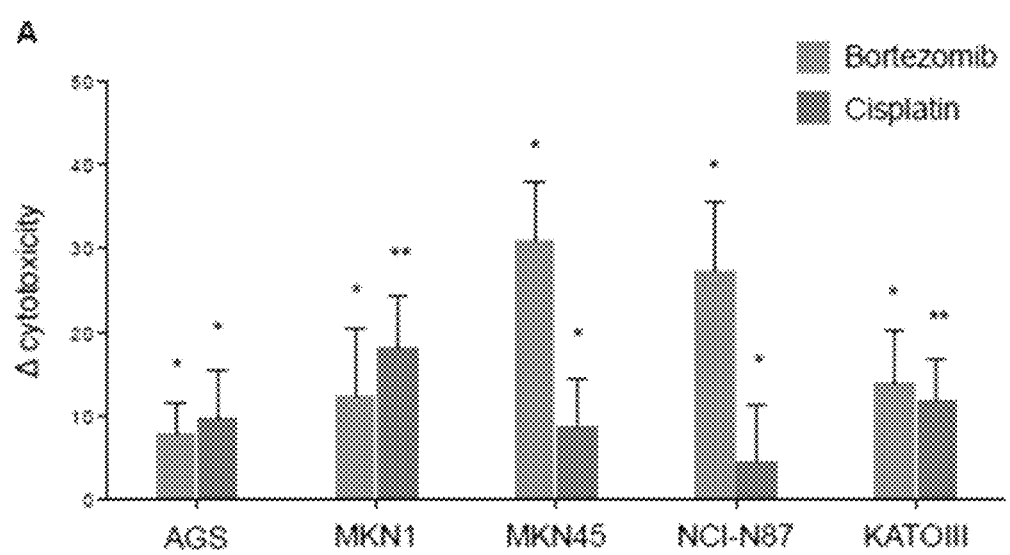
FIG. 6A shows results of measuring cytotoxicity using bortezomib or cisplatin to confirm the drug resistance induced by CD44 after PS exposure (10 μm diameter, 500 ppm, 4 weeks) and confirming the increase of A cytotoxicity in AGS, MKN1, MKN45, NCI-N87 and KATOIII cell lines.
Figure 6B:
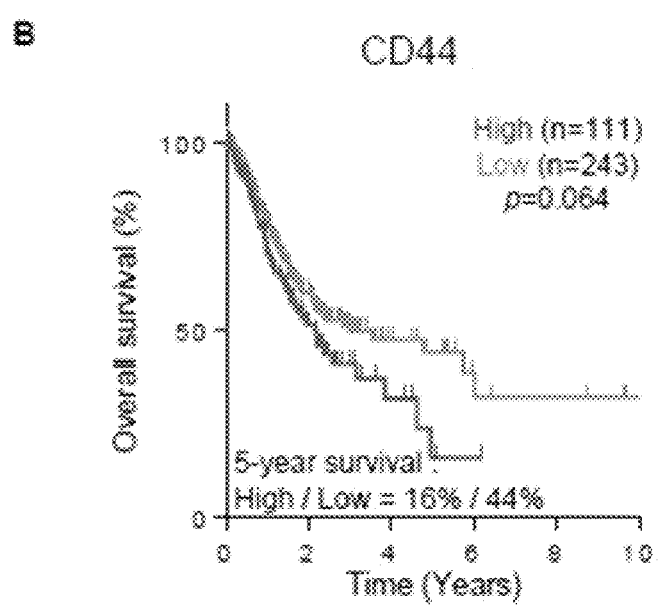
FIG. 6B shows results of confirming that the TCGA-STAD datasets with high CD44 expression showed a tendency of poor 5-years OS (P=0.064) (P-value: log rank t-test).

To assess the drug resistance due to CD44, cytotoxicity was measured using bortezomib or cisplatin. Then Δcytotoxicity was calculated as followings, "Δ cytotoxicity=cytotoxicity with PS—cytotoxicity without PS". FIG. 6A demonstrated increase of Δ cytotoxicity (* P<0.05, ** P<0.005). The TCGA-STAD datasets with high CD44 expression showed a tendency of poor 5-year OS (P=0.064) (FIG. 6B).

As upregulation of programmed death-ligand 1 (PD-L1) is reported to mediate potent immunosuppressive effects in tumor microenvironments, flow cytometry analysis was performed to confirm the change in PD-L1 expression in gastric cancer cells treated with PS for 4 weeks.

Figure 7A:
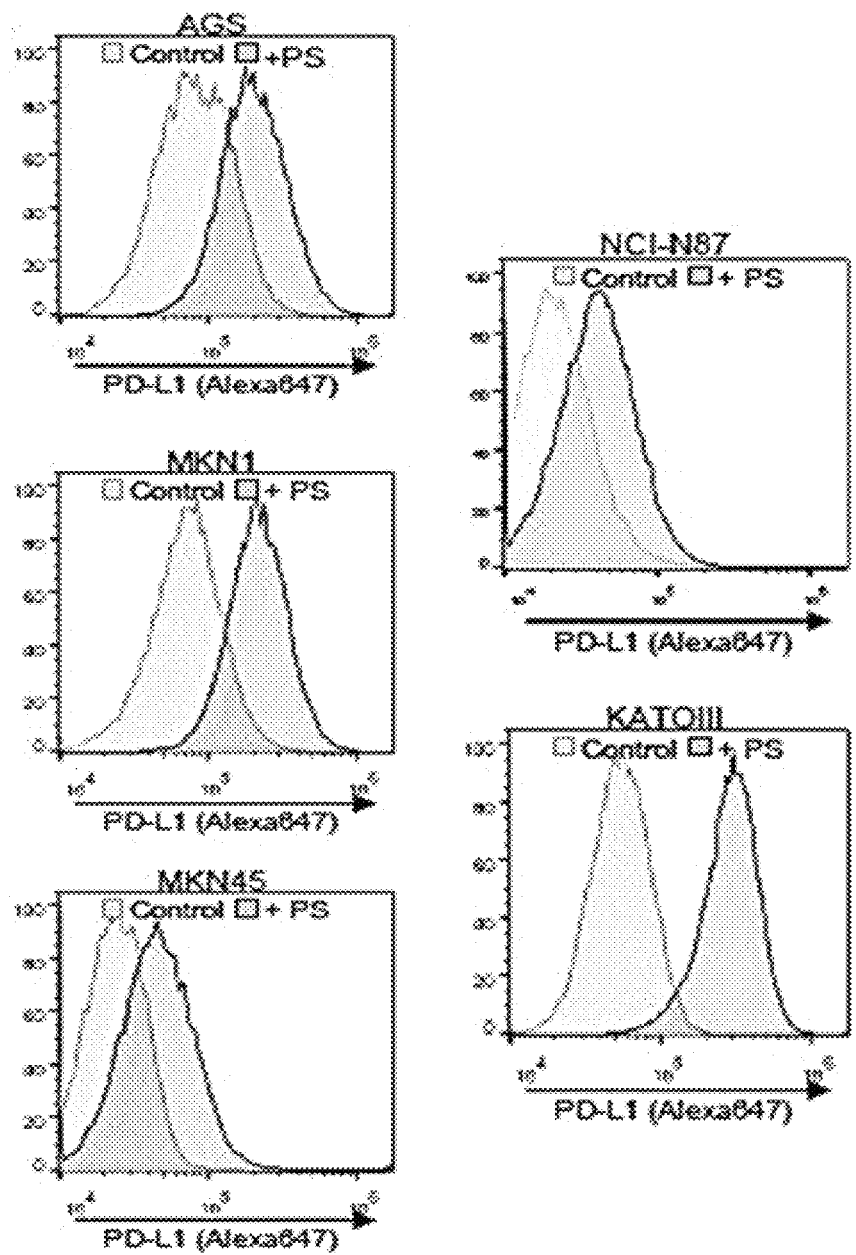
FIG. 7A shows flow cytometry histograms of PD-L1 expression in gastric cancer cell-lines and PS exposure for 4 weeks dramatically increased PD-L1 expression in all cell lines.
Figure 7B:
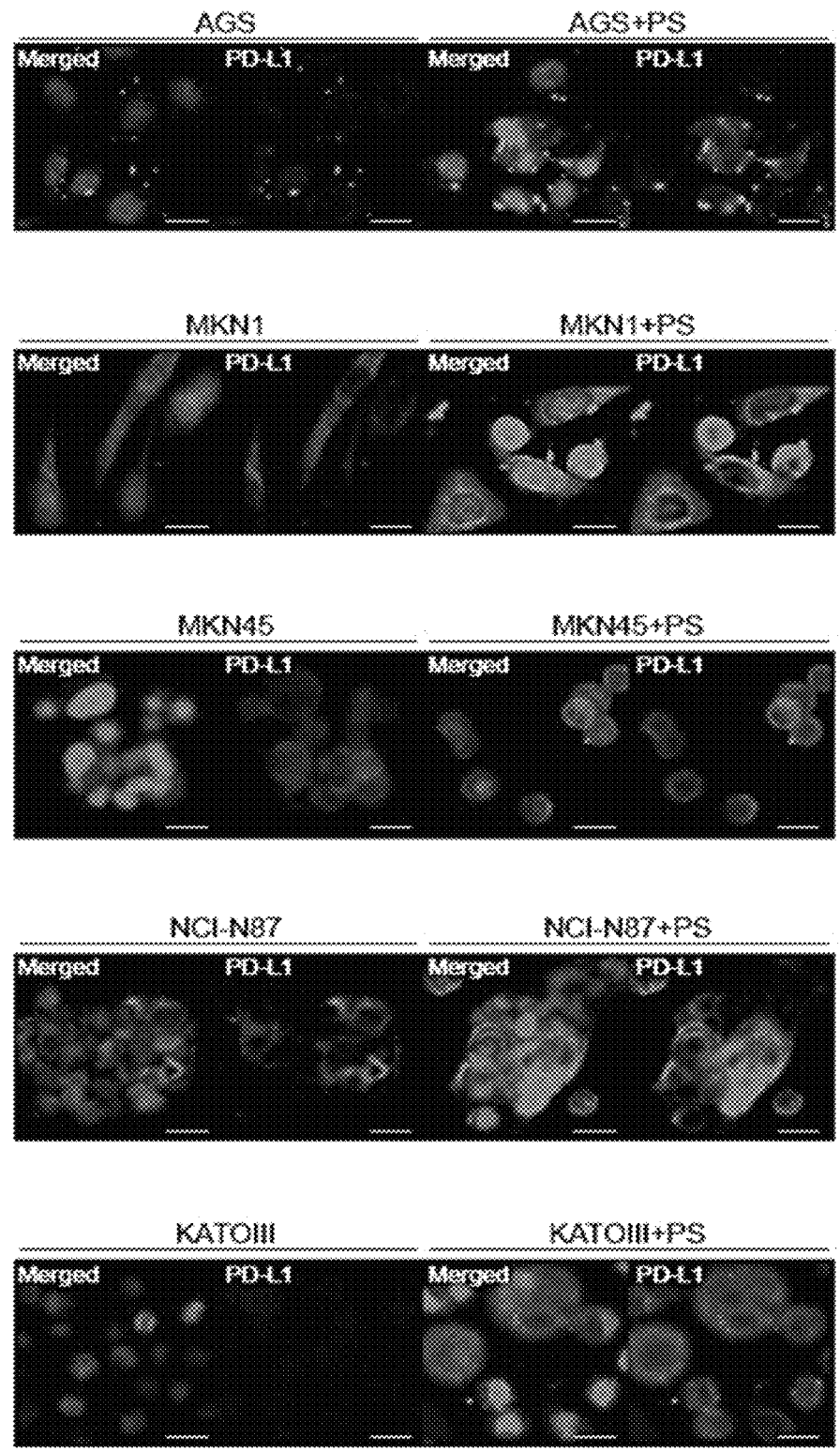
FIG. 7B shows immunofluorescence staining of PD-L1 in gastric cancer cells with/without PS (Magnification 40×, Scale bar: 20 μm)
Figure 7C:
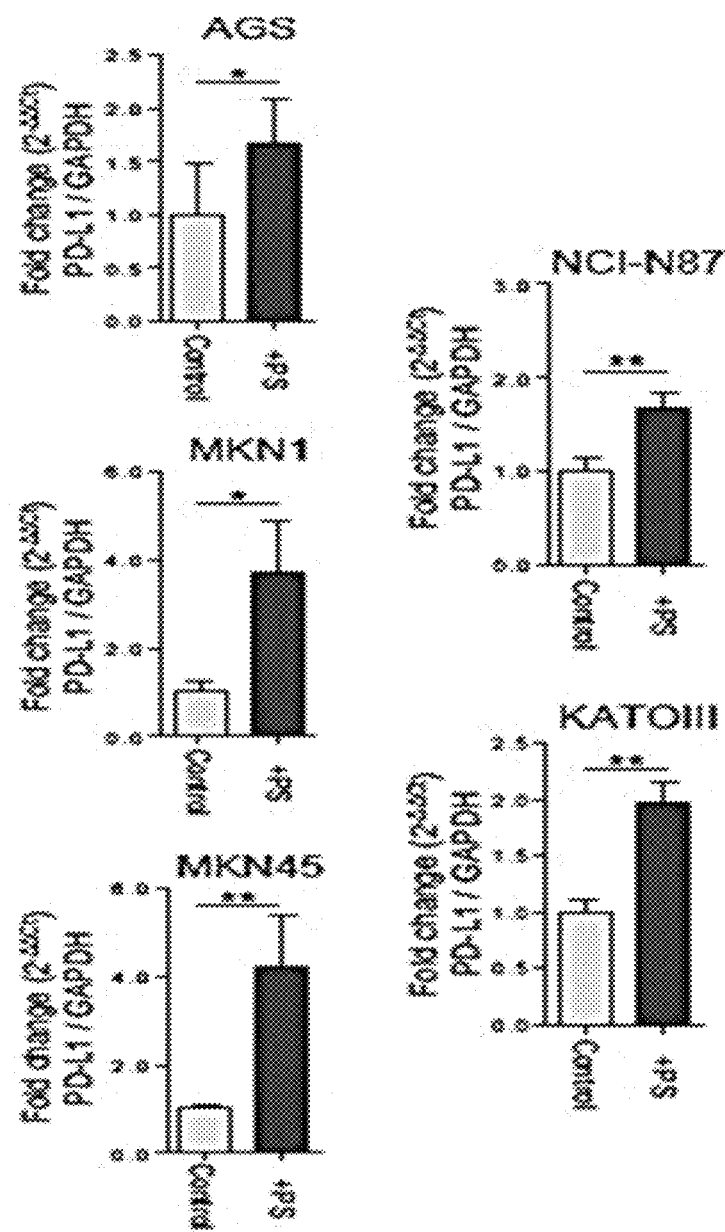
FIG. 7C shows qPCR results of mRNA level of PD-L1 expression (mean±SD, *P<0.05, **P<0.005, student's t-test).

Flow cytometry results indicated that PD-L1 expression was elevated for AGS, MKN1, MKN45, NCI-N87 and KATOIII cell lines (FIG. 7A). These results were confirmed by immunohistochemistry (FIG. 7B) and qPCR (FIG. 7C) and the fold increases were 1.67, 3.70, 4.23, 1.69, and 1.98 in AGS, MKN1, MKN45, NCI-N87, and KATOIII cells, respectively.

Figure 8A:
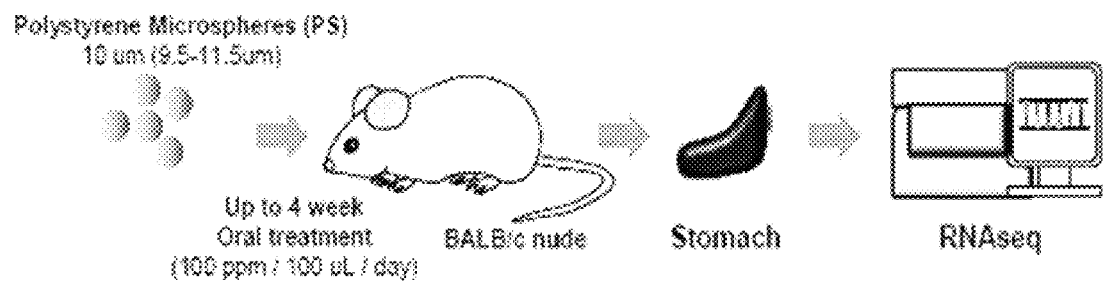
FIG. 8A shows schematic of the experimental procedures and BALB/c nude mice were exposed to 100 ppm/100 μL of PS for 4 weeks, and RNAseq was performed on the extracted stomach tissues.
Figure 8B:
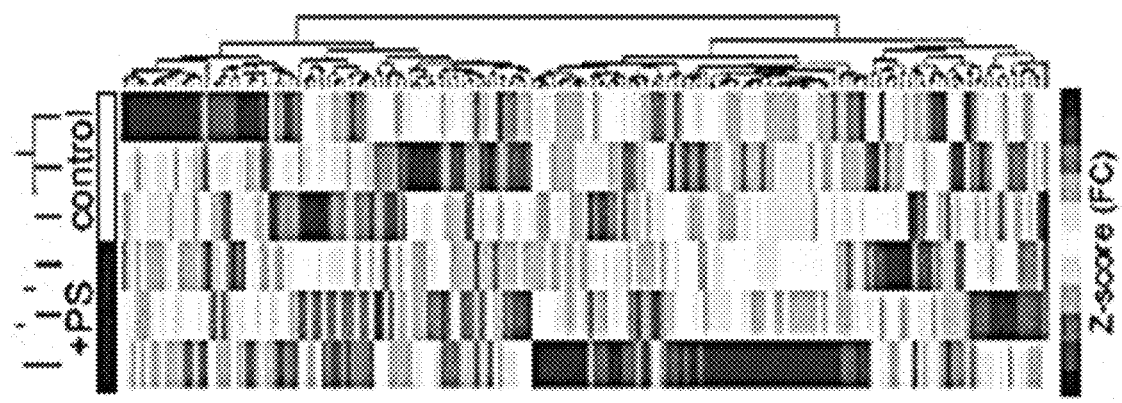
FIG. 8B shows heat map showing the RNA-seq analysis results and PS exposure induced gene expression changes in normal stomach tissues.
Figure 8C:
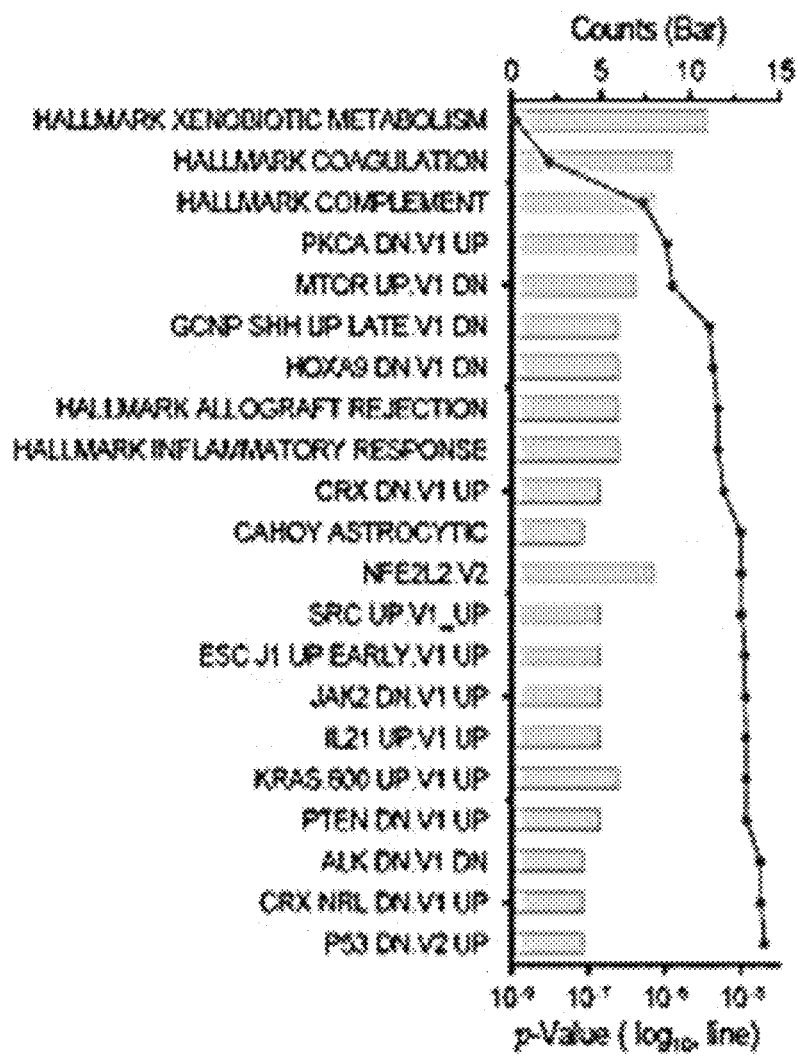
FIG. 8C shows gene set enrichment analysis using MSigDB and the experimental gene set overlap plenty of Hallmark and Oncogenic Signatures set.

RNAseq was performed using mouse stomach tissue 4 weeks after exposure of PS (FIG. 8A) and 194 (cut off fold change>2, P<0.05) significantly altered genes were identified in the PS exposure group compared to the control group (FIG. 8B).

Gene set enrichment analysis using MSigDB identified the genes in cancer hallmark (H) and oncogenic signatures (C6) set. To identify the effect of PS exposure to OS in patients, 145 genes that were common between the PS-exposed mouse model and the 354 patients in the TCGA-STAD dataset were identified (FIG. 8D).

To examine whether the change in OS correlates with changes in expression of these genes, the significantly expressed prognostic factors were identified based on a FPKM value>1 and log-rank p value<0.001, and gene overlapped by MSigDB H and C6.

Figure 8D:
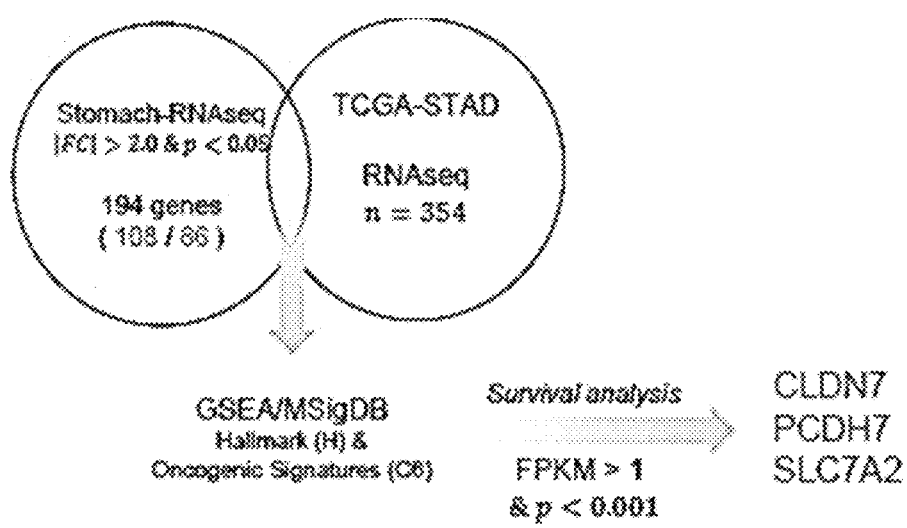
FIG. 8D shows schematic diagram showing the comparison of genes identified by RNAseq of PS-exposed mice and the TCGA-STAD RNAseq gastric cancer patient dataset (354 patients) and six candidate genes were found by correlating the overall survival values to the 145 genes examined.

Finally, 3 genes, SLC7A2, PCDH7, and CLDN7, were identified (FIG. 8D).

Figure 8E:
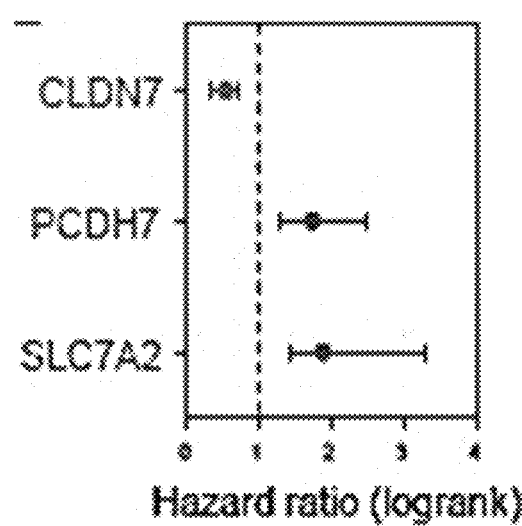
FIG. 8E shows the hazard ratio and among the six gene candidates, the fold changes in gene expression in the gastric 10 cancer patients were consistent with the murine RNAseq results, and three candidate genes with malignant effects on overall survival were found to be significant: CLDN7, PCDH7, and SLC7A2, and error bars represent the 95% confidence interval (CI) of the hazard ratio (HR)
Figure 8F:
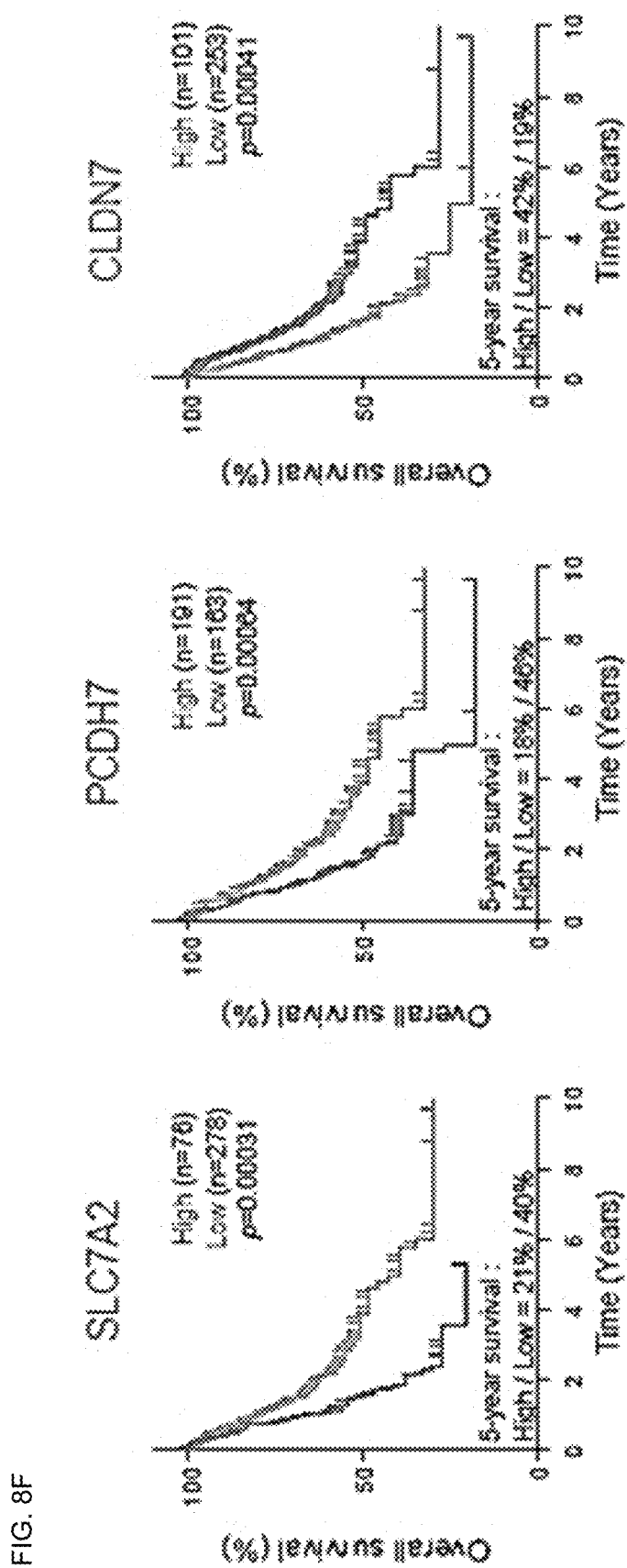
FIG. 8F shows Kaplan-Meier plots showing the overall survival of patients expressing the three major candidate genes from the TCGA-STAD patient data and increased SLC7A2 and PCDH7 and decreased CLDN7 expression dramatically correlated with the overall survival of gastric cancer patients (p-value: log rank t-test).

Next, it was confirmed hazard ratio for 3 common genes; SLC7A2 (HR=1.4250-3.281, P=0.00031), PCDH7 (HR=1.284-2.487, P=0.00064), and CLDN7 (HR=0.3497-0.7396, P=0.00041) (FIG. 8E).

An increase of 2.42-fold SLC7A2, 2.08-fold PCDH expression, and decrease of CLDN7 were observed in mouse RNAseq datasets. In the TCGA-STAD datasets, high expression of SLC7A2 (P=0.00031) or PCDH (P=0.00064), and low expression of CLDN7 (P=0.00041) showed poor 5-year OS.

Disruption of the circadian clock was known as cancer hallmarks and in fact, as shown in FIG. 8B, it was confirmed the decrease of NPAS2 expression (FC: −2.02) and the increase of NR1 D1 expression (FC: 2.80) in RNAseq data.

Figure 9A:
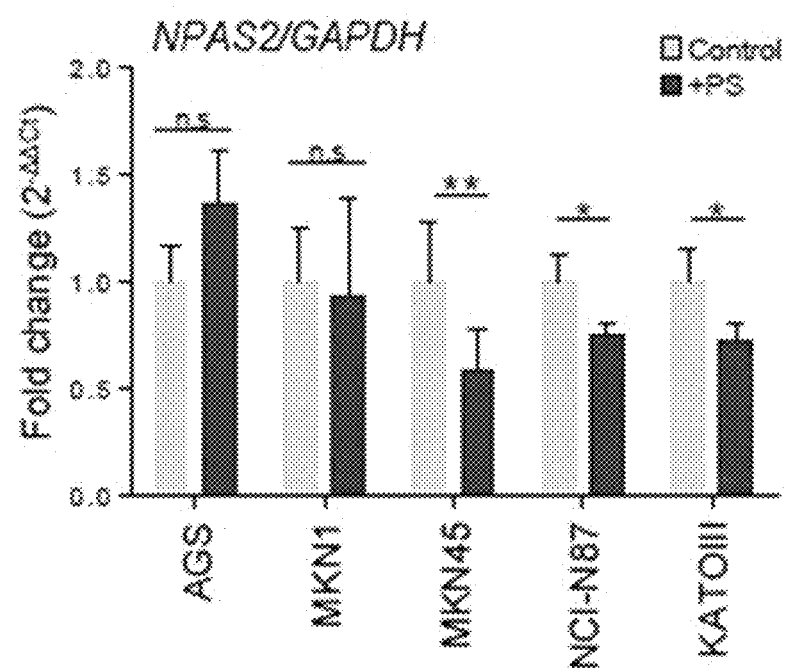
FIG. 9A shows that the qPCR analysis of NPAS2 mRNA expression and NPAS2 decreased following PS exposure (mean±SD *P<0.05, *P<0.005, Student's t-test, n.s., not significant)
Figure 9B:
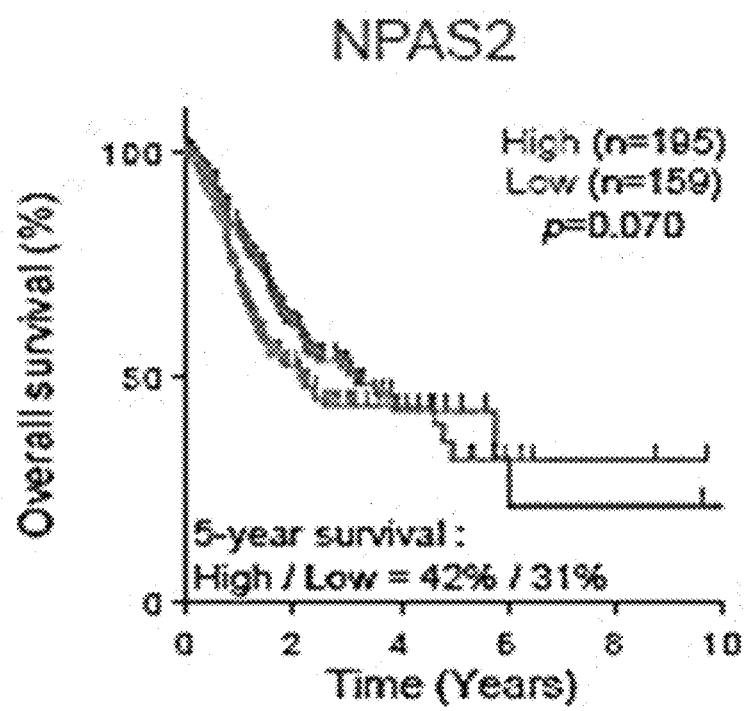
FIG. 9B shows that in TCGA-STAD datasets, low expression of NPAS2 showed poor 5-years overall survival (OS) rates.
Figure 9C:
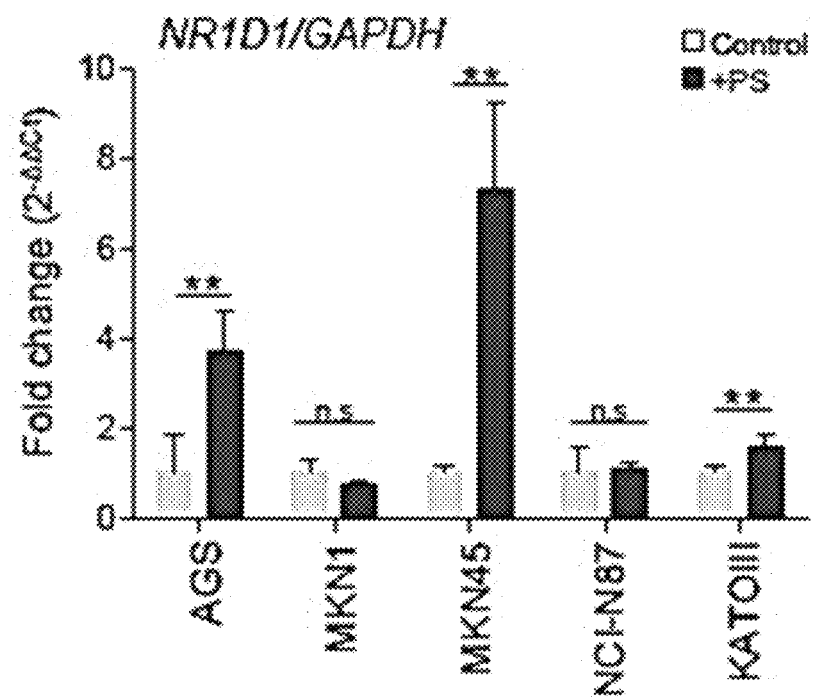
FIG. 9C shows the qPCR analysis of NR1D1 mRNA expression and NR1 D1 increased following PS exposure (mean±SD, *P<0.05, ** P<0.005, student's t-test, n.s., not significant)
Figure 9D:
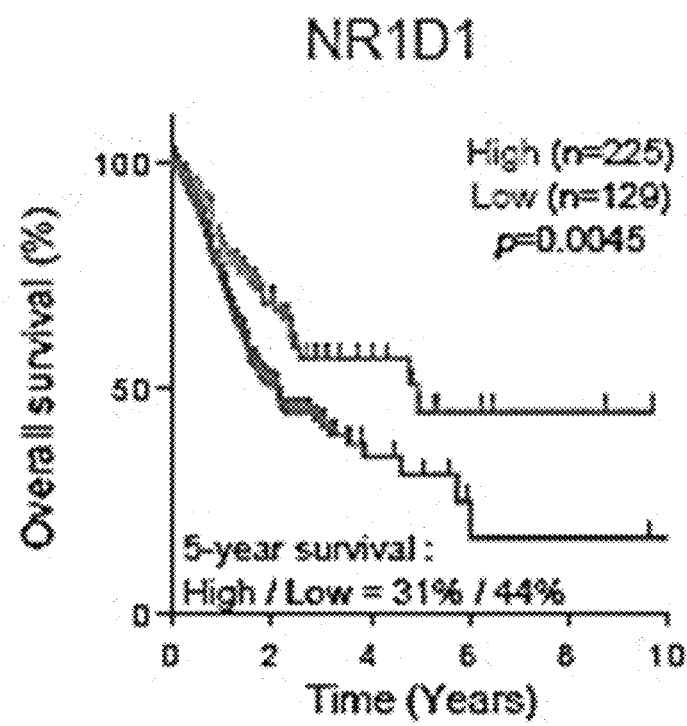
FIG. 9D shows that in TCGA-STAD datasets, high expression of NR1 D1 showed poor 5-years OS (P-value: log rank t-test)

Decrease of mRNA expression of NPAS2 in MKN45, NCI-N87, and KATOIII cells following PS exposure was also found (**P<0.005, * P<0.05) (FIG. 9A). The mRNA expression of NR1D1 increased for AGS, MKN45, KATOIII cell lines (** P<0.005) (FIG. 9C).

It was confirmed that low expression of NPAS2 (P=0.070) and high expression of NR1 D1 (P=0.0045) showed poor 5-year OS in TCGA-STAD datasets.

Next, it was confirmed whether PS exposure induces changes of methylation.

Figure 9E:
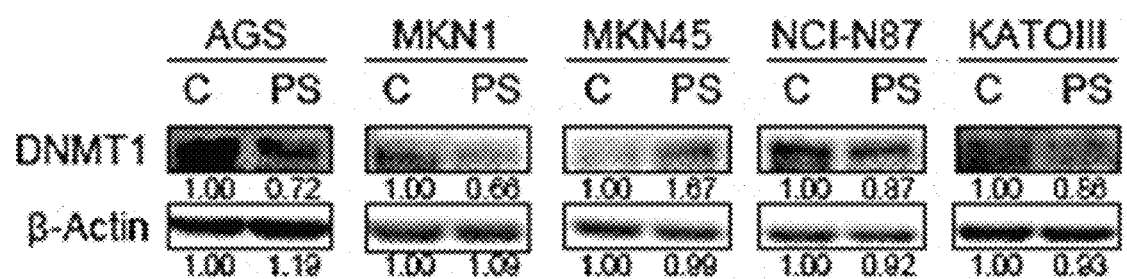
FIG. 9E shows western blot analysis of DNMT1 expression in cells with/without PS and DNMT1 decreased following PS exposure (P-value: log rank t-test)
Figure 9F:
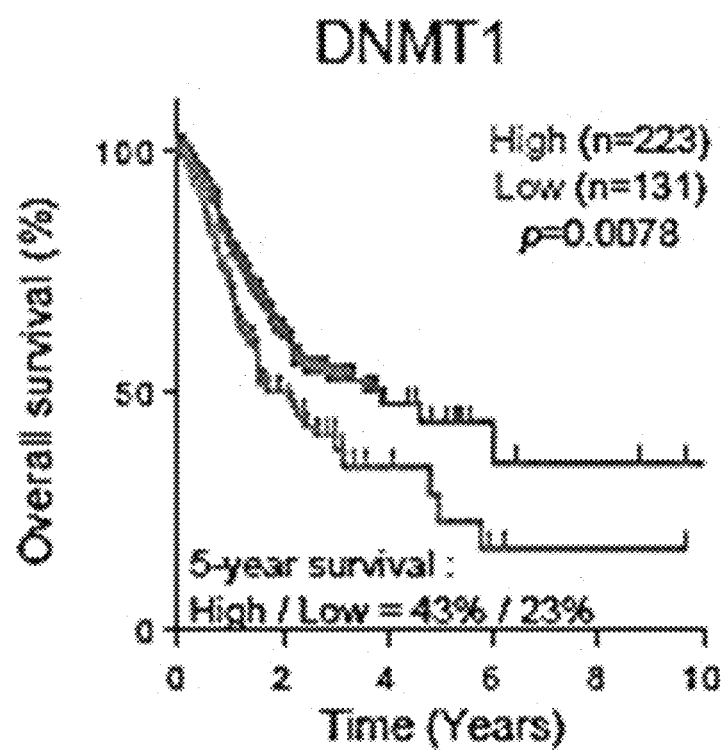
FIG. 9F shows that in TCGA-STAD datasets, low expression of DNMT1 showed poor 5-years OS (P-value: log rank t-test).

The western blot results indicated protein level of DNMT1 decreased in AGS, MKN1, N45, and KATOIII cells (FIG. 9E) and as shown in FIG. 9F, in TCGA-STAD datasets, low expression of DNMT1 showed poor 5-year OS.

According to the present invention, it was confirmed that the expression level of CD44, E-cadherin, N-cadherin, PD-L1, NPAS2, NR1D1, DNMT1, SLC7A2, PCDH7 and CLDN7 was changed in cancer cell lines and animal models treated with polystyrene microspheres which are the one type of microplastic for 4 weeks, and malignancy was induced due to an increase in proliferation, migration and invasion of cancer cells by the change in the expression level of the gene, and 5-year overall survival rates in gastric cancer patients decreased and thus the genes may be provided as a biomarker composition for predicting the prognosis of cancer malignancies by exposure to microplastics.

While the present invention has been particularly described with reference to specific embodiments thereof, it is apparent that this specific description is only a preferred embodiment and that the scope of the present invention is not limited thereby to those skilled in the art. That is, the practical scope of the present invention is defined by the appended claims and their equivalents.

What is claimed is:

1. A method of detecting changes in protein expression in gastric cancer cells exposed to microplastic, comprising:
   culturing gastric cancer cell lines obtained from subjects in medium;
   treating the cultured gastric cancer cell lines with 500 ppm of the microplastic for 4 weeks; and
   detecting protein levels of CD44, E-cadherin, N-cadherin, and PD-L1 (programmed death-ligand 1) in the cultured gastric cancer cell lines treated with the microplastic.

2. The method of claim 1, wherein the microplastic is.

* * * * *

SEQUENCE LISTING

<160> NUMBER OF SEQ ID NOS: 14

<210> SEQ ID NO 1
<211> LENGTH: 24
<212> TYPE: DNA
<213> ORGANISM: Artificial Sequence
<220> FEATURE:
<223> OTHER INFORMATION: GAPDH Forward

<400> SEQUENCE: 1
gcctcaagat catcagcaat gcct                                          24

<210> SEQ ID NO 2
<211> LENGTH: 24
<212> TYPE: DNA
<213> ORGANISM: Artificial Sequence

```
<220> FEATURE:
<223> OTHER INFORMATION: GAPDH Reverse

<400> SEQUENCE: 2
tgtggtcatg agtccttcca cgat                                          24

<210> SEQ ID NO 3
<211> LENGTH: 21
<212> TYPE: DNA
<213> ORGANISM: Artificial Sequence
<220> FEATURE:
<223> OTHER INFORMATION: N-cadherin Forward

<400> SEQUENCE: 3
agaggcttct ggtgaaatcg c                                             21

<210> SEQ ID NO 4
<211> LENGTH: 20
<212> TYPE: DNA
<213> ORGANISM: Artificial Sequence
<220> FEATURE:
<223> OTHER INFORMATION: N-cadherin Reverse

<400> SEQUENCE: 4
tggaaagctt ctcacggcat                                               20

<210> SEQ ID NO 5
<211> LENGTH: 19
<212> TYPE: DNA
<213> ORGANISM: Artificial Sequence
<220> FEATURE:
<223> OTHER INFORMATION: CD44 Forward

<400> SEQUENCE: 5
ccaatgcctt tgatggacc                                                19

<210> SEQ ID NO 6
<211> LENGTH: 21
<212> TYPE: DNA
<213> ORGANISM: Artificial Sequence
<220> FEATURE:
<223> OTHER INFORMATION: CD44 Reverse

<400> SEQUENCE: 6
tctgtctgtg ctgtcggtga t                                             21

<210> SEQ ID NO 7
<211> LENGTH: 20
<212> TYPE: DNA
<213> ORGANISM: Artificial Sequence
<220> FEATURE:
<223> OTHER INFORMATION: PD-L1 Forward

<400> SEQUENCE: 7
ttgggaaatg gaggataaga                                               20

<210> SEQ ID NO 8
<211> LENGTH: 21
<212> TYPE: DNA
<213> ORGANISM: Artificial Sequence
<220> FEATURE:
<223> OTHER INFORMATION: PD-L1 Reverse

<400> SEQUENCE: 8
ggatgtgcca gaggtagttc t                                             21
```

-continued

```
<210> SEQ ID NO 9
<211> LENGTH: 22
<212> TYPE: DNA
<213> ORGANISM: Artificial Sequence
<220> FEATURE:
<223> OTHER INFORMATION: NR1D1 Forward

<400> SEQUENCE: 9
ctggactcca acaacaacac ag                                              22

<210> SEQ ID NO 10
<211> LENGTH: 20
<212> TYPE: DNA
<213> ORGANISM: Artificial Sequence
<220> FEATURE:
<223> OTHER INFORMATION: NR1D1 Reverse

<400> SEQUENCE: 10
ggggatggtg ggaagtaggt                                                 20

<210> SEQ ID NO 11
<211> LENGTH: 20
<212> TYPE: DNA
<213> ORGANISM: Artificial Sequence
<220> FEATURE:
<223> OTHER INFORMATION: NPAS2 Forward

<400> SEQUENCE: 11
gtatcacgcc tctccttggg                                                 20

<210> SEQ ID NO 12
<211> LENGTH: 20
<212> TYPE: DNA
<213> ORGANISM: Artificial Sequence
<220> FEATURE:
<223> OTHER INFORMATION: NPAS2 Reverse

<400> SEQUENCE: 12
attacaggag gggctaggca                                                 20

<210> SEQ ID NO 13
<211> LENGTH: 23
<212> TYPE: DNA
<213> ORGANISM: Artificial Sequence
<220> FEATURE:
<223> OTHER INFORMATION: ACE2 Forward

<400> SEQUENCE: 13
cattggagca agtgttggat ctt                                             23

<210> SEQ ID NO 14
<211> LENGTH: 22
<212> TYPE: DNA
<213> ORGANISM: Artificial Sequence
<220> FEATURE:
<223> OTHER INFORMATION: ACE2 Reverse

<400> SEQUENCE: 14
gagctaatgc atgccattct ca                                              22
```